(12) United States Patent
Van Remortel et al.

(10) Patent No.: US 10,294,377 B2
(45) Date of Patent: May 21, 2019

(54) ULTRA FINE NEPHELINE SYENITE POWDER AND PRODUCTS FOR USING SAME

(71) Applicant: Unimin Corporation, New Canaan, CT (US)

(72) Inventors: Scott Van Remortel, Bakersville, NC (US); Frank Cangelosi, Southbury, CT (US); Jerry William Janik, Bridge North (CA)

(73) Assignee: Covia Holdings Corporation, Independence, OH (US)

( * ) Notice: Subject to any disclaimer, the term of this patent is extended or adjusted under 35 U.S.C. 154(b) by 0 days.

(21) Appl. No.: 15/943,645

(22) Filed: Apr. 2, 2018

(65) Prior Publication Data

US 2018/0223114 A1 Aug. 9, 2018

Related U.S. Application Data

(63) Continuation of application No. 15/155,455, filed on May 16, 2016, now abandoned, which is a
(Continued)

(51) Int. Cl.
*C08K 3/34* (2006.01)
*C09D 5/03* (2006.01)
(Continued)

(52) U.S. Cl.
CPC .................. *C09D 7/61* (2018.01); *A61K 8/26* (2013.01); *A61Q 3/02* (2013.01); *C01B 33/26* (2013.01);
(Continued)

(58) Field of Classification Search
CPC ... C09D 7/61; C09D 7/69; C09D 7/68; C09D 5/033; C09D 11/037; C09D 17/004;
(Continued)

(56) References Cited

U.S. PATENT DOCUMENTS 2,261,884 A 11/1941 Koenig
2,262,951 A 11/1941 Lyle
(Continued)

FOREIGN PATENT DOCUMENTS

GB 1297622 11/1972
JP 63158246 7/1988
(Continued)

OTHER PUBLICATIONS

Bath, Frank, Article titled Consistent Milling on a Nano Scale, Ceramic Industry, Feb. 2005.
(Continued)

*Primary Examiner* — Pegah Parvini
(74) *Attorney, Agent, or Firm* — Rankin, Hill & Clark LLP

(57) ABSTRACT

Specifically identified products are produced using powder formed from particles of a naturally occurring organic oxide mineral with substantially no free silica, preferably nepheline syenite, where the powder is essentially dry with a moisture content of less than 0.8% and has a controlled maximum particle size with 99.9% of the particles of the powder having a particle size of less than 10 microns defined as "fine grain ultra-fine" powder, which fine grain ultra-fine powder is preferably less than 6 microns, and where the fine grain ultra-fine powder comprises 3-25% by weight of the identified product.

8 Claims, 25 Drawing Sheets

|  | PRODUCT A |
|---|---|
| 99.9% < | 6.0 μm |
| MEAN | 1.9 μm |
| BRIGHTNESS (tappi) | 92 |
| % OIL ABSORPTION | 34 |
| % MOISTURE | 0.7 |
| pH VALUE | 10.7 |
| Mohs | 6.0 |

Related U.S. Application Data continuation of application No. 14/481,657, filed on Sep. 9, 2014, now abandoned, which is a continuation of application No. 11/803,093, filed on May 11, 2007, now Pat. No. 8,858,699, which is a continuation-in-part of application No. 11/599,514, filed on Nov. 14, 2006, now abandoned.

(60) Provisional application No. 60/906,386, filed on Mar. 12, 2007, provisional application No. 60/830,562, filed on Jul. 13, 2006.

(51) Int. Cl.
| | | |
|---|---|---|
| C09D 7/40 | (2018.01) | |
| C09D 7/61 | (2018.01) | |
| C09D 17/00 | (2006.01) | |
| C09D 101/18 | (2006.01) | |
| C09D 11/037 | (2014.01) | |
| C09D 133/06 | (2006.01) | |
| C01B 33/26 | (2006.01) | |
| A61Q 3/02 | (2006.01) | |
| A61K 8/26 | (2006.01) | |

(52) U.S. Cl.
CPC ............... *C08K 3/34* (2013.01); *C09D 5/033* (2013.01); *C09D 7/68* (2018.01); *C09D 7/69* (2018.01); *C09D 11/037* (2013.01); *C09D 17/004* (2013.01); *C09D 101/18* (2013.01); *C09D 133/06* (2013.01); *A61K 2800/412* (2013.01); *Y10T 428/2982* (2015.01)

(58) Field of Classification Search
CPC .... C09D 101/18; C09D 133/06; C01B 33/26; C08K 3/34
See application file for complete search history.

(56) References Cited

U.S. PATENT DOCUMENTS

| | | | |
|---|---|---|---|
| 2,269,912 A | 1/1942 | Ladoo et al. | |
| 2,478,645 A | 8/1949 | Thiess | |
| 2,765,074 A | 10/1956 | Diamond | |
| 2,871,132 A | 1/1959 | Hummel | |
| 3,044,619 A | 7/1962 | Knolle | |
| 3,079,309 A | 2/1963 | Wainer | |
| 3,326,701 A | 6/1967 | Von Freyhold | |
| 3,389,002 A | 6/1968 | Huffcut | |
| 3,486,706 A | 12/1969 | Weyand | |
| 3,721,066 A | 3/1973 | Teller | |
| 3,904,074 A | 9/1975 | Hoffman et al. | |
| 3,917,489 A | 11/1975 | Waters, Jr. | |
| 3,942,990 A | 3/1976 | Engstrom | |
| 3,998,624 A | 12/1976 | Harris et al. | |
| 4,028,289 A | 6/1977 | Brown | |
| 4,036,505 A | 7/1977 | Floyd et al. | |
| 4,130,423 A | 12/1978 | Chastant et al. | |
| 4,183,760 A | 1/1980 | Funk et al. | |
| 4,191,671 A | 3/1980 | Kataoka et al. | |
| 4,242,251 A | 12/1980 | Aishima et al. | |
| 4,267,089 A | 5/1981 | Brown | |
| 4,396,431 A | 8/1983 | Seeney et al. | |
| 4,468,473 A | 8/1984 | Drolet et al. | |
| 4,551,241 A | 11/1985 | Saverse et al. | |
| 4,639,576 A | 1/1987 | Shoemaker et al. | |
| 4,640,797 A | 2/1987 | Goguen | |
| 4,663,226 A | 5/1987 | Vajs et al. | |
| 4,743,625 A | 5/1988 | Vajs et al. | |
| 4,781,671 A | 11/1988 | Pober et al. | |
| 4,850,541 A | 7/1989 | Hagy | |
| 4,869,786 A | 9/1989 | Hanke | |
| 4,871,789 A | 10/1989 | Martinez | |
| 4,883,714 A | 11/1989 | Stockl et al. | |
| 4,885,832 A | 12/1989 | English | |
| 4,979,686 A | 12/1990 | Szegvari et al. | |
| 5,066,330 A | 11/1991 | Holcombe, Jr. et al. | |
| 5,080,293 A | 1/1992 | Szegvari et al. | |
| 5,153,155 A | 10/1992 | Kohut | |
| 5,199,656 A | 4/1993 | Szegvari et al. | |
| 5,236,499 A | 8/1993 | Chervenak et al. | |
| 5,380,356 A | 1/1995 | Gundlach et al. | |
| 5,423,490 A | 6/1995 | Zampini | |
| 5,530,057 A | 6/1996 | Humphrey et al. | |
| 5,686,507 A | 11/1997 | Hermele et al. | |
| 5,709,909 A | 1/1998 | Leibfarth et al. | |
| 5,866,646 A | 2/1999 | Radosta | |
| 5,883,029 A | 3/1999 | Castle | |
| 5,961,943 A | 10/1999 | Komatsu et al. | |
| 6,074,474 A | 6/2000 | Broome et al. | |
| 6,218,012 B1 | 4/2001 | Rota et al. | |
| 6,543,710 B2 | 4/2003 | Konetzka et al. | |
| 6,569,923 B1 | 5/2003 | Slagter | |
| 6,596,837 B2 | 7/2003 | Hogge et al. | |
| 6,739,456 B2 | 5/2004 | Svoronos et al. | |
| 6,790,904 B2 | 9/2004 | White et al. | |
| 6,793,875 B1 | 9/2004 | Shaw et al. | |
| 6,905,634 B2 | 6/2005 | Burnell-Jones | |
| 7,008,513 B2 | 3/2006 | Davenport et al. | |
| 7,751,150 B2 | 7/2010 | Horio | |
| 7,757,976 B2 | 7/2010 | Schlesinger et al. | |
| 8,858,699 B2 | 10/2014 | Van Remortel | |
| 2002/0013401 A1 | 1/2002 | Friel et al. | |
| 2002/0137872 A1 | 9/2002 | Schneider et al. | |
| 2002/0173384 A1 | 11/2002 | Hogge et al. | |
| 2002/0173597 A1 | 11/2002 | Zarnoch et al. | |
| 2003/0056696 A1 | 3/2003 | Fenske et al. | |
| 2003/0085383 A1 | 5/2003 | Burnell-Jones | |
| 2003/0085384 A1 | 5/2003 | Burnell-Jones | |
| 2003/0215770 A1 | 11/2003 | Sekino et al. | |
| 2003/0224174 A1 | 12/2003 | White et al. | |
| 2003/0229157 A1 | 12/2003 | Schneider et al. | |
| 2004/0068048 A1 | 4/2004 | Giles et al. | |
| 2004/0087433 A1 | 5/2004 | Herold | |
| 2004/0175407 A1 | 9/2004 | McDaniel | |
| 2005/0019574 A1 | 1/2005 | McCrary | |
| 2005/0059765 A1 | 3/2005 | Finch et al. | |
| 2005/0167534 A1 | 8/2005 | Tomikawa et al. | |
| 2005/0214534 A1 | 9/2005 | Adamo et al. | |
| 2006/0068314 A1 | 3/2006 | Kawata | |
| 2006/0075930 A1 | 4/2006 | Wang et al. | |
| 2006/0078748 A1 | 4/2006 | Ambrose et al. | |
| 2006/0081371 A1 | 4/2006 | Duenckel et al. | |
| 2006/0140878 A1 | 6/2006 | Cornelius et al. | |
| 2006/0160930 A1 | 7/2006 | Schneider | |
| 2006/0234026 A1 | 10/2006 | Huusken | |
| 2006/0235113 A1 | 10/2006 | Dorgan et al. | |

FOREIGN PATENT DOCUMENTS

| | | |
|---|---|---|
| WO | 2005/116137 A1 | 12/2005 |
| WO | 2007/123674 | 11/2007 |

OTHER PUBLICATIONS

Brochure regarding Air Classifiers, Sturtevant, Inc. Copyright 2004.
Brochure regarding Air Classifiers, Sturtevant, Inc. Copyright 1999.
MINBLOC, Physical and Chemical Properties Information Brochure, Oct. 2001.
MINBLOC, Antiblocking Additives, Information Brochure, 2001.
MINBLOC, Antiblocking Additives, Technical Data, Jun. 1988.
International Search Report in connection with International Application Numbr PCT/US2007/015848, Filed Jul. 12, 2007; Dated Dec. 6, 2007.
"Nepheline Syenite" from Wikipedia, Sep. 2006.
International Search Report dated Dec. 26, 2007 (Appln. No. PCT/US07/15855; filed Jul. 12, 2007).
Unimin Corporation. Minex Functional Fillers and Extenders Technical Data. May 2001, pp. 1 and 2.
Ibrahim, et al. Dry Magnetic Separation of Nepheline Syenite Ores. May 15, 2002.

(56) References Cited

OTHER PUBLICATIONS

C.J. Koenig, "Some Fundamental Properties of Nepheline Syenite"; Journal of the American Ceramic Society; Dec. 1939; vol. 22, Issue 1-12, pp. 35-38.
Union Process, Inc, 2004 Brouchure entitled "Dry Grinding Attritor".
European Search Report dated Jun. 10, 2009 for Appln. No. 07796807.1, filed Jul. 12, 2007 (PCT/US2007/015855).
European Office Action dated Sep. 10, 2009, issued in corresponding European Appln. No. 07796807.1, filed Jul. 12, 2007.
Office action dated Aug. 4, 2014 in corresponding European Application No. 07796807.1, filed Jul. 12, 2007.
U.S. Appl. No. 12/823,313.
U.S. Appl. No. 12/985,035.
U.S. Appl. No. 12/985,071.
U.S. Appl. No. 12/215,643.
U.S. Appl. No. 12/080,655.
U.S. Appl. No. 12/948,386.
U.S. Appl. No. 12/237,628.
U.S. Appl. No. 11/803,093.
U.S. Appl. No. 12/012,884.
U.S. Appl. No. 12/794,879.

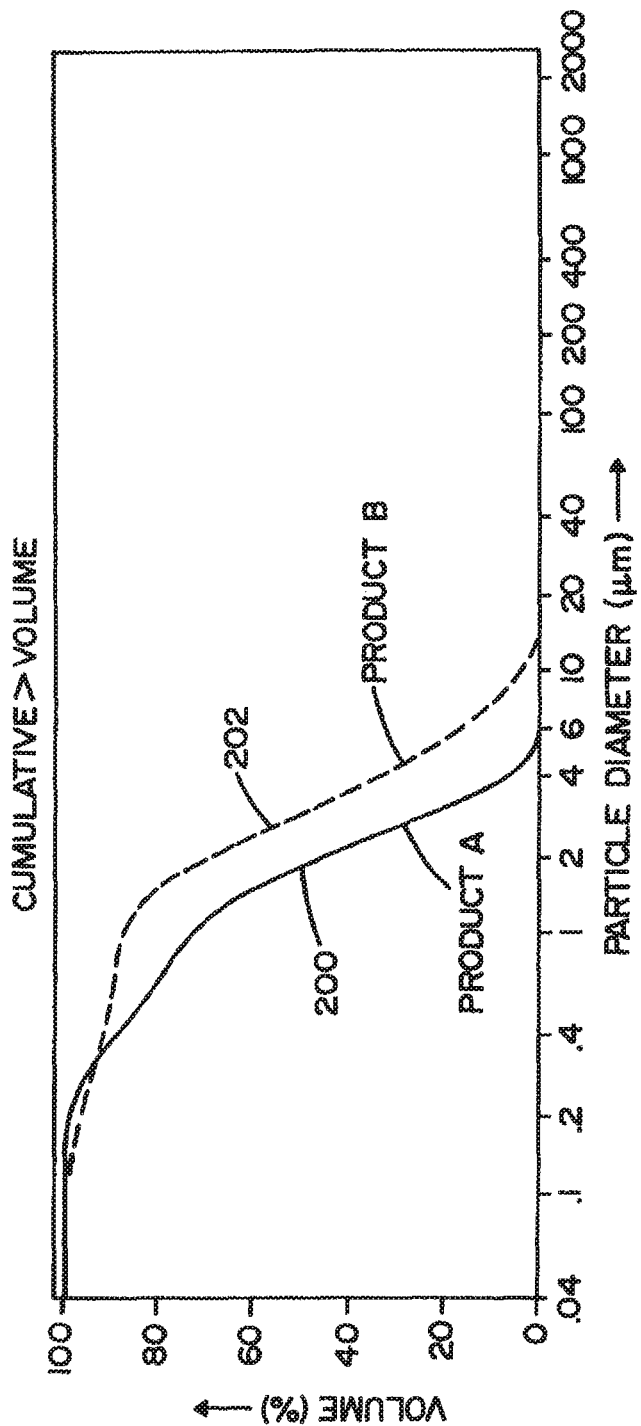

|  | PRODUCT A |
|---|---|
| 99.9% < | 6.0 μm |
| MEAN | 1.9 μm |
| BRIGHTNESS (tappi) | 92 |
| % OIL ABSORPTION | 34 |
| % MOISTURE | 0.7 |
| pH VALUE | 10.7 |
| Mohs | 6.0 |

ULTRA FINE NEPHELINE SYENITE POWDER AND PRODUCTS FOR USING SAME

CROSS REFERENCE TO RELATED APPLICATIONS

The present application is a continuation application of U.S. Ser. No. 15/155,455 filed May 16, 2016 (now abandoned), which is a continuation application of U.S. Ser. No. 14/481,657 filed Sep. 9, 2014 (now abandoned), which is a continuation application of U.S. Ser. No. 11/803,093 filed May 11, 2007 (now U.S. Pat. No. 8,858,699), which is a continuation-in-part (CIP) application of U.S. Ser. No. 11/599,514 filed Nov. 14, 2006 (now abandoned) and the applications are hereby incorporated herein by reference into this application and also claims priority upon U.S. provisional patent application Ser. No. 60/830,562 filed on Jul. 13, 2006; and U.S. provisional patent application Ser. No. 60/906,386 filed on Mar. 12, 2007 and both applications are hereby incorporated herein by reference into this application.

This application relates to the art of a processed powder formed from a natural occurring mineral and more particularly to a novel, ultra fine nepheline syenite powder that obtains unique physical characteristics and several applications of the novel nepheline syenite powder including, but are not limited to, coatings, such as clear, ultraviolet cured and powder coatings. In addition, the application discloses novel products using ultra fine nepheline syenite powder as a substitute for distinctly different fillers or additives.

BACKGROUND

Standard ground nepheline syenite in particulate form has been a commercial product for many years. Indeed, nepheline syenite powder in particulated form has been used extensively to make industrial compounds and to instill enhanced properties in liquid coatings, ceramics, glass, etc. For illustrations of representative products or compounds employing standard processed particulate nepheline syenite, the following United States patents are incorporated by reference. Consequently, the general properties and procedures for using existing nepheline syenite particles need not be repeated.

| Koenig | 2,261,884 | use as flux in ceramic |
|---|---|---|
| Lyle | 2,262,951 | color ingredient in glass |
| Thiess | 2,478,645 | porcelain glaze |
| Hummel | 2,871,132 | glazing compound |
| Huffcut | 3,389,002 | heat and corrosion resistant coating |
| Weyand | 3,486,706 | binder for grinding agent |
| Waters | 3,917,489 | ceramic flux |
| Harris | 3,998,624 | source of metal aluminum silicate |
| Brown | 4,028,289 | inorganic filler |
| Chastant | 4,130,423 | natural silicate for slag formation |
| Funk | 4,183,760 | alumina ceramic |
| Aishima | 4,242,251 | alumina silicate filler |
| Seeney | 4,396,431 | inorganic binder |
| Drolet | 4,468,473 | SiO$_2$ source |
| Shoemaker | 4,639,576 | electrode coating |
| Goguen | 4,640,797 | polymer filler |
| Vajs | 4,743,625 | vitrifying material |
| Holcombe | 5,066,330 | refractory filler |
| Kohut | 5,153,155 | nonplastic filler |
| Slagter | 6,569,923 | polymer cement |
| White | 6,790,904 | liquid coating |

Disclosures contained in the patents listed above are incorporated by reference as background technology. Particulate nepheline syenite is used in diverse products and for many applications. However, the disclosed nepheline syenite powder does not have the total property array of the novel nepheline syenite powder constituting a first aspect of the invention. Furthermore, these background patents do not have or suggest the applications made available only by creation and use of the novel nepheline syenite powder. These novel products, with unique properties made possible by the newly developed, novel nepheline syenite powder, constitute a second or additional aspect of the inventive technology of this application.

Other uses of standard, ground nepheline syenite have been recently suggested. Representative examples of such newer applications of ground nepheline syenite are disclosed in the following United States patent publications:

| Schneider | 2002/0137872 | scratch resistant coating |
|---|---|---|
| Zarnoch | 2002/0173597 | filler in resin powder |
| Fenske | 2003/0056690 | filler for polymer cement |
| Burnell | 2003/0085383 | suspending filler |
| Burnell | 2003/0085384 | heat curable resin |
| White | 2003/0224174 | filler in liquid coating |
| Scheider | 2003/0229157 | scratch resistant powder coating |
| Giles | 2004/0068048 | filler for rubber |
| Finch | 2005/0059765 | filler for plastic coating |
| Adamo | 2005/0214534 | extender for curable composition |
| Duenckel | 2006/0081371 | sintering aid |
| Schneider | 2006/0160930 | corrosion resistant coating |
| Dorgan | 2006/0235113 | filler for polymer |

These prior descriptions illustrate uses, or proposed uses, of ground nepheline syenite. Such additives have been used for many industrial components and as a filler, an extender or another component of consumer materials, such as coatings. However, the totality of this prior and extensive background technology has not led the mining industry to develop the novel nepheline syenite powder of the present invention or the uses of such novel nepheline syenite powder in both known and newly discovered applications. These new uses form novel products that are enhanced physically by use of ultra fine nepheline syenite powder having the characteristics of the novel form of nepheline syenite.

In addition to the background technology incorporated by reference in the section above, general background information regarding the use of ground nepheline syenite forms technical background to understand, practice and employ the present invention. In the glass and ceramic manufacturing industry, ground nepheline syenite provides alkalis that act as a flux to lower the melting temperature of a glass and/or ceramic mixture thereby promoting fast melting and fuel savings in the manufacturing process. In glass making, ground nepheline syenite also supplies aluminum which gives improved thermal endurance, increases chemical durability and increases resistance to scratching and breaking of the resulting vitrified product. Furthermore, ground nepheline syenite and larger grain nepheline syenite powder are used as a filler or extender in paints, coatings, plastics and paper. It is a desirable material because it contains virtually no free silica and still functions as effectively as a free silica based filler or extender. The material is an inorganic oxide having mechanical characteristics similar to the free silica materials for which it is used as a substitute in various industries. These mechanical properties of ground nepheline syenite are realized by the use of a fine grain particulate form of nepheline syenite, which is sometimes a powder that has a grain size greater than about 15-60 microns. These known ground and powdered nepheline syenite are quite abrasive for manufacturing equipment. Consequently the granular nepheline syenite has a high tendency to abrade and erode quite rapidly equipment used in processing the various compounds, even compounds incorporating the fine grain powder of the prior art. It has been determined that by reducing the fine grain size of any inorganic oxide material, such as nepheline syenite, the abrasive properties of the material are reduced. It is common to provide ground nepheline syenite with a relatively small grain size for the purpose of allowing effective dispersion of the product aided by the use of nepheline syenite powder. The advantage of dispersing fine grain nepheline syenite in the carrier product is discussed in several patents, such as Gundlach U.S. Pat. No. 5,380,356; Humphrey U.S. Pat. No. 5,530,057; Hermele U.S. Pat. No. 5,686,507; Broome U.S. Pat. No. 6,074,474; and, McCrary Publication No. US 2005/00019574. These representative patent publications show fine grain nepheline syenite and are incorporated by reference herein as background information regarding the present invention. These disclosures illustrate the advantages of providing this inorganic oxide in a very fine grain size for a variety of applications. In US Publication 2005/00019574 there is a discussion that microcrystalline silica is a preferred filler in plastic. Ground nepheline syenite from Unimin Corporation, New Canaan, Conn., is thus provided as a fine grain silica deficient silicate in the form of a sodium potassium alumino silicate. The particles of this nepheline syenite are finely divided and have a grain size in the range of about 2 to about 60 microns. This widely used commercial product having this grain size and wide particle size distributions has been sold as an additive that provides the nepheline syenite properties. Thus, materials employing ground nepheline syenite as a filler or extender and also as a glass or ceramic additive, has heretofore used fine grain nepheline syenite from Unimin Corporation having a controlled grain size less than about 60 microns. The produced nepheline syenite powder could not be produced with a controlled grain size of less than 15 microns. By using special equipment, Unimin Corporation has now been able to produce an ultra fine particle size nepheline syenite powder with a maximum particle size of less than about 10 microns; however, to make this material it is necessary to provide specialized grinding and milling equipment or drastically changed equipment operation. Consequently, in the past the standard, ground nepheline syenite used in various limited industries has been a nepheline syenite with a grain size controlled to be less than about 60 microns. In recent years, Unimin Corporation has developed a nepheline syenite powder which has a controlled grain size less than about 15 microns. This was believed to be the absolute industry limit for ultra fine nepheline syenite powder and forms the background. From experience, the industry believed that a limit of 15 microns was the ultimate grain size capability because the technology of producing nepheline syenite powder with controlled size less than 15 microns often involved moisture content which caused the particles to actually agglomerate into larger particles and defeat the primary purpose and cost of producing the smaller ultra fine particles. With respect to nepheline syenite powder, the terms "particle" and "grain" are used interchangeably. This is further background of the industry to which the present invention is directed.

BRIEF DESCRIPTION

The primary aspect of the present invention is provision of a nepheline syenite powder having a grain or particle size of less than 6 microns and a moisture content of less than 0.8% by weight of powder. This particle grain size was heretofore believed to be impossible to obtain because of physical laws, such as a drastically increased reactive surface area, and a substantial tendency to agglomerate. Furthermore, there was a complete lack of equipment to produce such very small particles. There was no motivation for providing such particle size in face of the known technical impediments. However, when novel nepheline syenite powder was ultimately provided to the industry for use, it was found that the novel powder resulted in a low Einlehner Abrasive Value of less than 100 and, indeed, as low as 50 or less. It was discovered that the particle size of the novel nepheline syenite powder reduced wear to increase the longevity of manufacturing equipment, but it resulted in other physical advantages that enhance the end product. When these other advantages were discovered and recognized, the technology, motivation and reasons for producing the novel ultra fine nepheline syenite powder has been drastically altered. Experimental discoveries identified and resulted in the realization of the greater technical needs for the novel finer grain nepheline syenite powder. Thus, the present invention relates to the first aspect of controlling the particle size of nepheline syenite powder not only to obtain the advantages of fine grain nepheline syenite powder regarding the longevity of manufacturing equipment, but also to obtain physical characteristics of the product itself other than the common properties associated with ground and powdered nepheline syenite as has been used for many years in many different industries. In summary, the present invention involves a discovery of physical properties that can be obtained by further drastically reducing the grain or particle size of nepheline syenite.

The invention is a nepheline syenite powder with drastically reduced particle size to reduce abrasion and enhance dispersion and reduce settling. Such novel powder unexpectedly results in several recently discovered properties. These discovered properties were learned only by extensive experimentation and/or testing and after being able to obtain a powder with drastically reduced particle size.

It has been found that an ultra fine nepheline syenite powder useful as a substitute for other known particulate nepheline syenite to dramatically reduce wear on mechanical equipment could, with specifically controlled grain size limitations, introduce heretofore unknown and unobtainable physical properties in coatings, adhesives, sealants, inks and other products. Thus, the first aspect of the present invention provides a nepheline syenite powder with a novel particle or grain size whereby it greatly reduces wear, is easily dispersed in resin systems, drastically reduces settling, has a low oil absorption, has a natural wetting characteristic with a low moisture content, high pH, and a high brightness. By using the powder with a particle or grain size forming the first aspect of the present invention, coatings can be created by controlled, specific loading of the ultra fine nepheline syenite powder to increase block and abrasion resistance, increase clarity, increase the effect on gloss, increase hardness and stability of the coating. Consequently, nepheline syenite powder with a novel particle size has been found to enhance characteristics of the coatings in a manner not obtainable by larger grain nepheline syenite powder now available.

The present invention is primarily directed to ultra fine nepheline syenite powder having a very low particle size with low moisture content to prevent agglomeration and a low abrasive value for equipment. This novel ultra fine nepheline syenite powder has heretofore not been known to the industry and was not sought by the industry since the motivation for providing this particular material is the physical properties imparted to a product and discovered after the powder was available. The totality of characteristics or properties was not known in the industry to be properties obtainable by nepheline syenite powder. Furthermore, by developing a special ultra fine nepheline syenite powder, the novel powder can be used to create a large number of novel coatings and other applications which also constitute aspects of the invention. Consequently, the first aspect of the invention is the ultra fine nepheline syenite powder with a small particle size to reduce wear, increase dispersion, and decrease settlement and to obtain these various advantageous enhancements in diverse products. The second aspect of the invention is the actual products themselves. In many instances the products are actually novel for the fact that they employ nepheline syenite powder having a grain size less than about 10 microns. However, the ultra fine nepheline syenite powder to enhance these characteristics was the heretofore unavailable nepheline syenite powder having a grain size of less than about 6 microns.

Nepheline syenite powder having larger particle or grain size has been used as a filler and/or extender in paint, coatings, plastics, rubber and other materials. The nepheline syenite powder imparts a variety of physical properties and technical enhancements to these systems, such as improved scrub and abrasion resistance in coatings. It has been discovered that the novel nepheline syenite powder having controlled particle size developed as one aspect of the present invention offers surprisingly improved levels of optical performance while maintaining other critical performance properties of coating. Thus, the novel nepheline syenite powder is particularly beneficial for clear coatings. Another novel aspect of the present invention is its use to obtain properties attributed only to the novel nepheline syenite powder in various applications. The new powder has a considerably less abrasive effect on equipment than commercially available ultra fine nepheline syenite powder. It also provides substantial physical benefits in clear coatings, powdered coatings, ultraviolet cured coatings and other applications which benefits have been realized when compared to various products using commercially available nepheline syenite powder and other commercial fillers. One of the applications that has been found to benefit substantially by the use of the novel ultra fine nepheline syenite powder of the present invention is powder coatings, which may be clear or colored.

In accordance with the first aspect of the present invention, nepheline syenite powder is provided with controlled particle size where 99.9% of the particles are less than 6 microns. The term "less than" when defining a particle or grain size of the nepheline syenite powder has the known meaning that 99.9% of the particles in the powder have a size less than the stated size limitation. It, therefore, if not so stated, means that the "maximum" size of the particles is no greater than the stated size limitation. Thus, a powder with particles having a grain size less than 6 microns indicates that for at least 99.9% of the particles, there are a multitude of sizes with the upper size limitation being 6 microns. The particles do not necessarily have a fixed or uniform particle size. This novel powder has a moisture content of less than 0.8%. It has been found that such powder has an EAV of about 50 or less. The novel powder is processed without the addition of water. Furthermore, the oil absorption of this novel powder, under 14 ASTM D-281, is in the general range of 34%. This is a very low oil absorption property for the novel powder. The novel powder has a pH in the general range of 9-11 and has a grain size distribution of about 5-6 microns. Particle size distribution indicates that the particles, as previously stated, have a variety of sizes from a low value to a maximum value. The number of microns between these values is the "distribution" of grain size or particle size.

The ultra fine particle size material having a particle or grain size of less than about 6 microns has been proven successful in a coating with the powder used as a filler or extender, a clear coating, an ultra fine cured coating, a wood coating, a powdered coating including clear coating, automotive clear coating, coil coating, sealants, paper laminates for pictures and other structures and inks. All of these products have enhanced physical characteristics based upon the use of the ultra fine nepheline syenite powder with the novel grain size of less than 6 microns.

Nepheline syenite powder of the present invention drastically reduces wear on equipment processing the product using the novel inorganic mineral powder. By providing a grain size not heretofore available for nepheline syenite powder the Einlehner Abrasive Value (EAV) is substantially less than 100 and about 50 or less.

In accordance with another aspect of the invention, a novel final product is formed by using nepheline syenite powder having a grain size less than 15 microns. The products are novel because they do not now employ ultra fine nepheline syenite powder for the purpose of enhancing physical characteristics or properties. The ultra fine nepheline syenite powder of these final novel products includes the novel nepheline syenite powder having less than 6 microns as well as larger nepheline syenite powder having a grain size less than 15 microns. As a recapitulation, these new final products (such as coatings) are novel because they now use "ultra fine nepheline syenite powder" (less than 6 microns or less than 15 microns). Specific properties in certain products are actually more enhanced by employing the novel nepheline syenite powder having a grain size of less than 6 microns. However, the novelty of these commercial or final products is use of an "ultra fine nepheline syenite powder", i.e. a nepheline syenite having a grain size of less than 15 microns. In summary, some products provided in accordance with a derivative aspect of the invention are novel by using ultra fine nepheline syenite, i.e. a powder with a grain size less than 15 microns. Other new products are novel by using the novel powder having a grain size less than 6 microns. In both of these types of novel commercial or final products, the ultra fine grain nepheline syenite powder is loaded in the range of 12-20% by weight. These new products use the ultra fine nepheline syenite powder not only because it reduces the wear on manufacturing equipment and/or reduces settlement, but also because the powder imparts specifically discovered physical characteristics or properties, such as a controlled gloss. Thus, the several new products are novel due to the use of ultra fine nepheline syenite powder with a specific loading so that the powder results in enhanced physical characteristics of the coatings. The heretofore unrealized properties are due to the ultra fine nepheline syenite powder incorporated in high amounts to effect a drastic reduction in cost of the product. This is irrespective of the controlled grain size, such as less than 15 microns or the first novel concept of a grain size less than 6 microns. To distinguish the novel powder from powder with a grain size less than 15 microns, the invention is broadly defined as a powder with a grain size less than 10 microns, but in practice it is a powder with a grain size less than 6 microns. Both are a small size not heretofore successfully produced and/or commercially available.

Some new products are novel because they have not heretofore used ultra fine nepheline syenite powder at all. They have not used a powder with a grain size less than 15 microns. These products have sometimes used ground nepheline syenite but have not employed ultra fine nepheline syenite powder. "Ultra fine nepheline syenite powder" is a powder with a controlled grain size less than 15 microns. The development of the ultra fine nepheline syenite powder with a grain size less than 6 microns has caused the art to identify a wide variety of applications of such powder, which applications have not heretofore been known to the trade. The new powder has been employed in products not now using nepheline syenite of any grain size and, indeed, in products not even using ground nepheline syenite.

The present development project has resulted in another group of new products that are enhanced by using ultra fine nepheline syenite powder with a loading of 10-20% by weight. These products have used nepheline syenite of a substantially greater grain size, such as ground nepheline syenite. Such products are new and novel. They have enhanced characteristics because they have a high loading of ultra fine nepheline syenite powder. This class includes ultraviolet cured coating, nitrocellulose lacquer, acrylic lacquer, solvent based cured varnish, aqueous coatings such as lacquer, acrylic urethane and other urethane coatings, and 100% solids coatings. These coatings are enhanced by using ultra fine nepheline syenite powder; however, they are further enhanced by using the novel nepheline syenite powder having a grain size of less than 6 microns. Additional products in this class of goods improved by using ultra fine nepheline syenite powder, other than coatings, are adhesives, sealants, inks and paper laminates for simulated wood of furniture and other structures. All of these applications or new products have been tested and have shown enhanced physical characteristics as will be explained in this disclosure. They are new and novel because they use ultra fine nepheline syenite powder having a grain size of less than 15 microns, but preferably they use the novel nepheline syenite powder having a grain size of less than 6-10 microns.

In accordance with another aspect of the present invention there is provided another group of commercial or final products including an ultra fine nepheline syenite powder. This group consists of clear liquid wood coating, clear liquid coating for flexible substrates, clear liquid coating for rigid substrates, nail polish, glass, metallurgical slag, refractory fillers, and pigment paste to make coatings.

A further aspect of the invention is a new product that now includes a finer grain ultra fine nepheline syenite powder. The product is selected from the class consisting of opaque liquid coatings, coatings of less than 10 microns in thickness, inks, powder coatings, ceramic bodies, glazes, plastic fillers, rubber fillers, color concentrates or pastes and sealants. These products use the novel finer grain ultra fine nepheline syenite powder to produce enhanced physical characteristics and properties as will be explained later.

In accordance with yet another aspect of the present invention, the novel finer grain ultra fine nepheline syenite powder is used to provide a product from the class consisting of clear coatings, sealants, paper laminates, aqueous coatings, solvent based coatings, UV cured coatings, water based coatings with resin free pigment paste, nitrocellulose clear lacquer, acrylic lacquer, clear solvent based acid cured varnish, aqueous lacquer, acrylic urethane coating, aqueous clear PUD urethane coatings, 100% solids clear UV coatings and powder coatings. Also, the novel nepheline syenite powder is used in a "concentrate", such as a paste or predispersant that is incorporated into polymer systems used as coatings, plastics or rubber articles. The loading or percent of powder added to the final product is carried by the concentrate into such product.

The primary object of the present invention is the provision of an ultra fine nepheline syenite powder having a controlled particle size where 99.9% of the particles are less than 6 microns. This novel ultra fine nepheline syenite powder has a moisture content of less than 0.7% and preferably about 0.6%. Essentially all of the particles will pass through a 500 mesh screen and have an Einlehner Abrasive Value (EAV) of less than 100. In accordance with another aspect of the present invention the nepheline syenite powder is processed without the addition of water and has a grain size distribution of less than about 5-6 microns, i.e. particles between about 0.30 to 6.0 microns.

A further object of the present invention is the provision of the novel ultra fine nepheline syenite powder, which is drastically smaller in grain size than prior ultra fine nepheline syenite powder.

Yet another object of the present invention is the provision of products, such as coatings, utilizing ultra fine nepheline syenite to obtain heretofore unobtainable physical properties for the product.

Another object of the present invention is the provision of the novel nepheline syenite powder having the novel controlled particle size and specific products using the novel ultra fine nepheline syenite powder.

A further object of the present invention is provision of a nepheline syenite powder with a grain size less than about 6 microns that is a highly bright material useable for filler applications in clear coatings and/or as an anti-block agent in polymer material. This powder can be formed into a concentrate and then dispersed into the coating or material.

In summary, the overall object of the present invention is the provision of a novel small grain, ultra fine nepheline syenite powder, products using this novel powder and products using either the small grain ultra fine nepheline syenite powder or a slightly larger grain ultra fine nepheline syenite powder, i.e. a powder having a particle size less than 10 microns. Some novel products use any ultra fine nepheline syenite powder, i.e. a powder with a grain size less than 15 microns, when prior commercial versions of such products did not use ultra fine grain nepheline syenite powder.

Still a further object of the present invention is (a) the use of a novel small grain ultra fine nepheline syenite powder in any product, (b) the use of finer grain ultra fine nepheline syenite in products heretofore using only ground nepheline syenite, and (c) the use of ultra fine nepheline syenite powder in a product that has not heretofore used nepheline syenite powder at all.

A further object of the invention is the provision of an ultra fine nepheline syenite powder with a controlled grain size of less than about 6 microns, which powder, when used for ultraviolet, clear or semi transparent coatings, results in a superior clarity compared to competitive fillers, can be used with up to about 20-25% loading, is UV transparent, is easily dispersed in low viscosity systems and increases film hardness and scratch resistance.

Yet a further object of the present invention is an ultra fine nepheline powder, as defined above, which powder, when used in a coating, retains weathering durability as does larger particle size powder, improves hardness and block resistance for kitchen and appliance applications, offers higher gloss than larger grain nepheline syenite powder while maintaining favorable oil absorption and bulk density characteristics. The novel powder has controlled particle top-size to minimize abrasion and equipment wear and has superior cost/performance balance versus expensive "nano" fillers. The use of the novel powder results in a cost reduction which is enhanced because higher loading is possible.

A basic object of the invention is provision of a nepheline syenite powder with a controlled grain size to result in a Einlehner Abrasive Value of less than 100 and preferably less than about 50.

A general object of the invention is provision of powder formed from naturally occurring organic oxide mineral with substantially no free silica, preferably nepheline syenite, used in specifically identified products, which powder is fine grain ultra-fine, i.e. having a controlled maximum particle size of less than 10 microns, and comprising 3-25% of the total weight of the products. Furthermore, the powder is essentially dry with a moisture content of less than 0.8% and substantially free of particles having particle size of less than 0.2 microns.

Another object of the invention is the provision of a coating containing nepheline syenite powder that is clear, hard, and resistant to scratches, and which is relatively inexpensive. If the coating is curable by exposure to ultraviolet radiation (i.e. is UV curable), another object of the invention is that the coating containing nepheline syenite powder be readily curable.

An overview object of the present invention is the provision of "finer grain" ultra fine nepheline syenite powder, which powder is made commercially obtainable by using a method which does not introduce water and/or moisture to the powder.

These and other objects and advantages will become apparent from the following description.

BRIEF DESCRIPTION OF THE DRAWINGS

FIG. 2 is a chart showing the size and particle size distribution for the novel ultra fine nepheline syenite powder identified as product A and another version of ultra fine nepheline syenite powder represented as product B for comparison of the two powders;

FIG. 3 is a table illustrating the grain size and medium grain size of both product A and product B;

DETAILED DESCRIPTION

Figure 1:
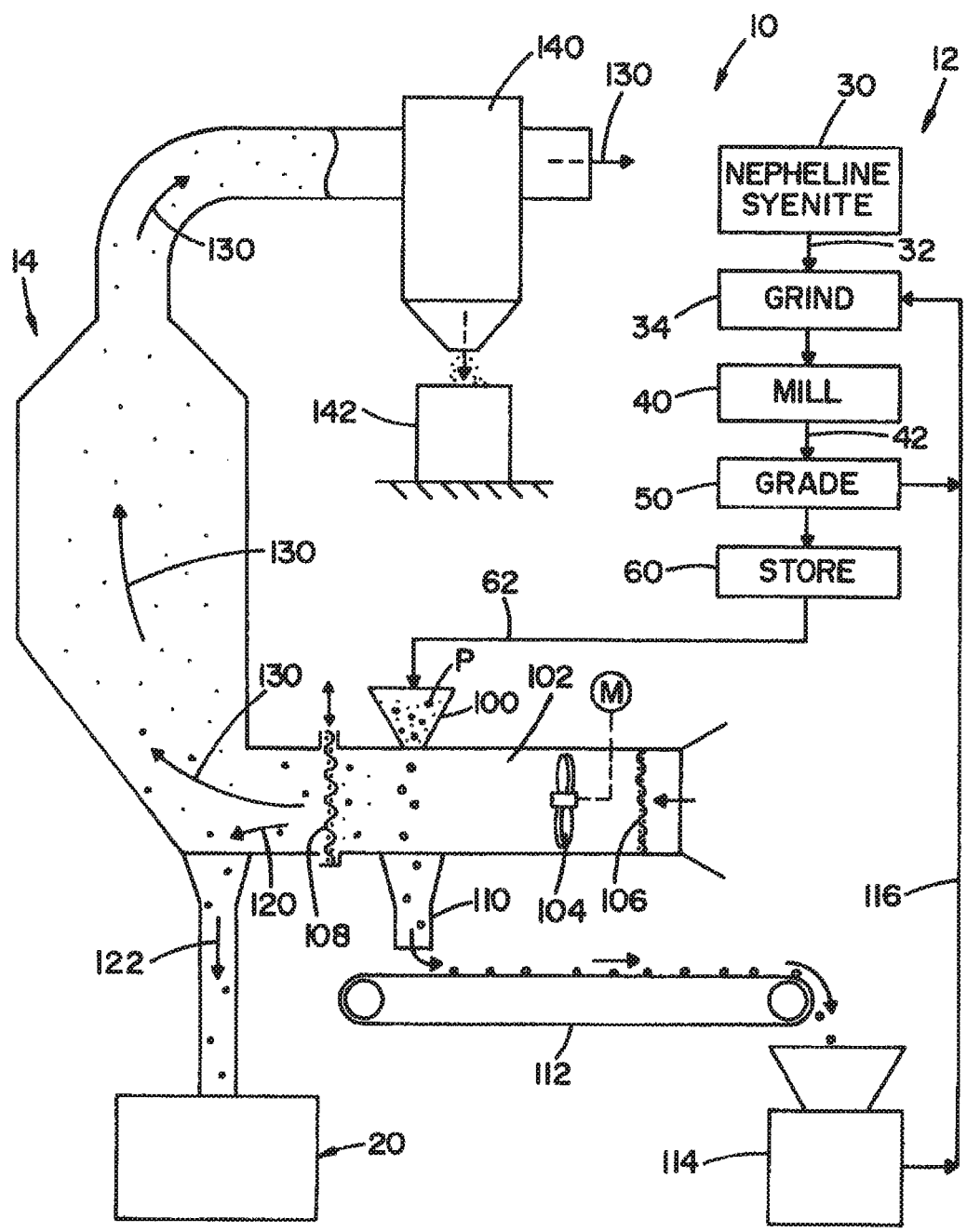
FIG. 1 is a combined block diagram and schematic diagram of representative equipment for producing ultra fine nepheline syenite powder.

The present invention is directed to ground nepheline syenite material which is converted into specific ultra fine nepheline syenite powder having a controlled grain size that has been proven to be instrumental in providing coatings with enhanced features, such as thinner films and finer pigment pastes. Furthermore, whenever a supplier needs to produce a coating that is thinner, higher gloss and less abrasive the novel "finer grain" ultra fine nepheline syenite powder with a grain size of less than 6 microns has proven to be extremely beneficial, indeed critical. In clear, ultraviolet cured and wood coatings requiring transparency, gloss and less package settlement, it has been found that ultra fine nepheline syenite powder with a controlled grain size of less than 6 microns, which is one aspect of the present invention, has been extremely beneficial. The novel nepheline syenite powder results in heretofore unobtainable physical characteristics in the many coatings. In addition, ultra fine nepheline syenite powder, especially the finer grain nepheline syenite powder having a grain size of less than 6 microns, has been proven to be a cost effective alternative to currently available, quite expensive nano size fillers or nano size particles. Such small particles are precipitated or reacted by expensive procedures. Consequently, the novel ultra fine nepheline syenite powder is a substitute for such costly minerals. It has been found that the physical properties obtained by ultra fine nepheline syenite powder, in general, is drastically enhanced by reduced grain size to less than 6 microns, accompanied by increased loading of the reduced grain size ultra fine nepheline syenite powder. These advantages of the primary aspect of the present invention, i.e. the novel finer grain ultra fine nepheline powder, are, in addition to and sometimes duplicative of, the advantages discussed in the introductory portion of the present disclosure. The disclosures establish the commercial merit of various aspects of the present invention. Indeed, there are distinct advantages of using ultra fine nepheline syenite powder in certain coatings and the novel finer grain ultra fine nepheline syenite in certain coatings and other products. But the most pronounced advantages are realized by the novel ultra fine nepheline syenite powder having a grain size of less than about 6 microns, i.e. the finer grain ultra fine nepheline syenite powder. Ultra fine nepheline syenite powder having a grain size of less than about 15 microns is known, but reducing the grain size to less than 10 microns and preferably less than 6 microns is not known. Such small size powder has not been commercially feasible prior to this invention. There was little known about the tremendous combinations of properties and characteristics to be imparted to products by the novel grain size reduction of the present invention. The concept of reducing the grain size of ultra fine nepheline syenite powder was not pursued and the advantages were not realized until the present inventive act of reducing the grain size all the way to less than 10 microns. The more critical advance is the drastic reduction of nepheline syenite powder to a grain size less than 6 microns.

Referring now to the drawings, wherein the showings are for the purpose of disclosing preferred embodiments and properties of the preferred embodiments and/or aspects of the present invention and not for the purpose of limiting same, FIG. 1 shows schematic equipment 10 represented by a number of steps and process components. Equipment 10 produces ultra fine nepheline syenite powder. Equipment 10 is merely representative of the manner by which the ultra fine nepheline syenite powder is produced. The method combines a dry milling section 12, shown schematically, and an air classifier section 14, also shown schematically. The dry milling and air clarifier sections produce ultra fine nepheline syenite powder with a controlled and specific grain size. The grain size is less than about 10 microns in the broad sense, but in the preferred sense the grain size of the powder is less than 6 microns. This is the novel feature to make a grain size less than 10 microns, i.e. less than 6 microns. This new grain size for nepheline syenite powder is distinctly novel over ultra fine nepheline syenite in general and is a size heretofore unobtainable by conventional methods used for commercial production of powdered nepheline syenite. In the method to produce the ultra fine nepheline syenite powder of the invention, mined nepheline syenite is loaded into supply bin 30. The grain size of the nepheline syenite is standard size available from the natural mineral deposit. This bulk natural nepheline syenite has a generally as mined consistency. It is transported by conveyor 32 into a standard mineral grinder. This grinder provides a standard ground nepheline syenite of the type now sold commercially. This ground mineral is like the nepheline syenite now used in a variety of industries, as explained in the introductory portion of this disclosure. The ground nepheline syenite has a standard grain size which is up to at least 500-1,000 microns. This ground mineral is used as a feed stock for the remaining components of equipment 10 shown in FIG. 1. In other words, normal standard ground nepheline syenite is the feed stock for use in producing the ultra fine nepheline syenite powder of the present invention. Feed stock created by grinder 34 is directed through line 36 into dry mill 40 which, therefore, operates without any added water. The dry mill reduces the size of the particles of the ground nepheline syenite into a powder with a grain size of about 60-100 microns maximum. Thus, the grain size is less than about 60-100 microns. This is a known product. This milled nepheline syenite powder formed from standard ground nepheline syenite is directed to outlets 42, having a grading screen 50 which passes powder having a generally fine grain size, such as a grain size that will pass through a 200 mesh screen. The fine powder has a maximum size substantially greater than 25 to 50 microns and it is accumulated in storage bin 60, which bin is an agitated and aerated storage bin to maintain dry powder P having a maximum grain size greater than about 25-50 microns. Moisture accumulation in the mineral is prevented. Thereafter, the milled nepheline syenite powder P in storage bin 60 is conveyed along line 62 by a combined screw and air conveyor which aerates and agitates the powder to maintain the powder fluidized and with a low moisture content, i.e. less than 0.7% and preferably about 0.6% by weight. The powder from storage bin 60 is carried through line 62 to input 100 of air classifier section 14. Powder P has a distribution of grain sizes from fines of less than 1.0 microns to a grain size of over 50-60 microns. This high grain size distinguishes powder P from "ultra fine nepheline syenite powder", which, by definition, has a grain size of less than about 15 microns. From input 100, powder P drops into separation chamber 102 having a high volume blower 104 supplied with processed air supplied through intake screen 106. Chamber 102 has a graded output screen of louver plate 108, which screen or plate is set to allow particles of powder P to pass through the air classifier, if the grain size of the particles is less than a selected value. In other words, the air velocity is high enough to carry particles of powder P through screen or plate 108 if they do not weigh too much. In practice, screen or plate 108 has a maximum size of 10 microns to produce a grain size less than ultra fine nepheline syenite powder. However, the preferred nepheline syenite powder of the present invention has a grain size of less than about 6 microns, which is a grain size heretofore unobtainable because of various manufacturing limitations and perceived obstacles. The screening must be extremely small while allowing capture by air from blower 104. This air velocity must be high to propel small grain powder through the classifier section. This novel powder is referred to as "finer grain" ultra fine nepheline syenite powder. Thus, screen or plate 108 is selected to pass grains having a size of less than 10 microns to produce a grain size less than normal ultra fine nepheline syenite powder. In accordance with the preferred embodiment and the basic novelty, the screen or plate is selected for about 6 microns to produce finer grain nepheline syenite powder and the blower is drastically increased to convey the small particles. Particles of incoming powder P, that are too large to pass screen or plate 108 and too heavy to be carried by the high flow of process air, drops through chute 110 to conveyor belt 112 for deposit into hopper 114. From this hopper, large particles in powder P are recirculated through milling section 12 by way of return line 116. The returned large particles of powder P are then reprocessed through the various components in the general milling section 12. Powder particles that pass through screen or plate 108 for the most part, drop into collector 20, as indicated by arrows 120 and 122. Process air flow created by blower 104 operated at a high speed is indicated by arrows 130. This high velocity air carries "fines", i.e. small particles less than about 0.2-0.5 microns. These small particles have a weight that will not allow them to drop into collector 20. Thus, air indicated by arrow 130 transports fines through the air classifier upward to accumulator 140, where the fines are intercepted and fall into bin 142 for ultimate disposal. Finer grain ultra fine nepheline syenite powder with a grain size controlled by screen or plate 108 is deposited in collector or bin 20. It is then bagged and sold for use to create the physical properties and obtain the advantages already explained. These and other advantages of finer grain ultra fine nepheline syenite powder and the preferred, novel powder with a grain size of less than 6 microns will be addressed hereinafter and, in some instances, have already been disclosed. The "finer grain ultra fine nepheline syenite powder" has a particle size of less than about 6 microns. Thus, the invention is a particle size substantially less than 15 microns, which is broadly stated as being less than 10 microns. But preferably the grain size is less than 6 microns to obtain the advantages described herein.

When screen or plate 108 is selected for a grain size of less than 6 microns, product A is produced by equipment 10. This powder is an ultra fine nepheline syenite powder having a maximum grain size of about 6 microns and a grain distribution as indicated by curve 200 in FIG. 2. This distribution is generally 4-5 microns. This powder is compared to a powder having a maximum grain of about 15 microns, i.e. product B. Particle distributions of products A and B are shown by curves 200, 202 in FIG. 2. The powders are explained in FIG. 3. Product B is a powder having a grain size and distribution as illustrated by curve 202 of FIG. 2. The maximum grain size of this powder is about 15 microns. Product A and product B are both ultra fine nepheline syenite powder, but they each have a specific controlled grain size. Product A is a powder with a grain size drastically smaller than the grain size of product B. Details of equipment 10 can be varied so long as the method disclosed is used to produce the finer grain ultra fine nepheline syenite powder, using a dry milling operation performed by a standard dry mill followed by an air classifier operation performed by a standard air classifier. The novelty is the adjustment of the equipment to obtain product A. The equipment and the method are not novel, but the use of such equipment to produce the novel product A with no need to use water is unique.

In accordance with the primary and first aspect of the invention, the ultra fine nepheline syenite powder has drastically reduced maximum grain size, i.e. less than 6 microns. At least 99.9% of all particles are less than 6.0 microns in size. This is a controlled grain size never available before. This novel finer grain ultra fine nepheline syenite powder, which is product A, has the capabilities of imparting distinct novelty and heretofore unobtained, physical properties to diverse receiving media, such as many coatings. When the particle size is reduced to the 6 micron level, product A has the unique physical, mineral properties, as set forth in FIG. 4. These properties involve a maximum grain size of about 6 microns. The term "maximum" in this disclosure is a standard term and means that more than 99.9% of the grain size are less than the stated maximum. Product A has a mean particle size of 1.9 microns and a brightness of 92, oil absorption of 34 and a percentage of moisture of 0.7. Indeed, low moisture content is critical and is preferably 0.4-0.8%. This low moisture is essential so that the particles do not agglomerate and, thus, create large multi-particle masses which would defeat the intended main purpose and basic advantage of the finer grain ultra fine nepheline syenite powder. Product A is basic, with a pH value of 10.7 and has a Mohs hardness of 6.0. All these physical characteristics or properties create a synergistic action for the preferred, novel ultra fine nepheline syenite powder, i.e. the finer grain nepheline syenite powder. In this manner, the novel powder can create several recently discovered beneficial physical properties in the end products, or receiving media, sometimes also referred to as a "product" or "products." Such properties have not heretofore been obtainable or they were not known to be obtainable by any filler or binder. This new vista of enhanced properties obtained by using finer grain ultra fine nepheline syenite powder, is evidence of the tremendous advance in the art caused by the discovery of advantages of a controlled small grain size for this mineral. The novel ultra fine nepheline syenite powder has a heretofore unobtainable grain size, i.e. a grain size less than 6 microns. Product A is a substantial advance in the art. In accordance with a second aspect of the present invention, as previously described, the use of novel product A and the use of product A or now existing product B in certain specific applications are also separately novel and create beneficial results not heretofore known. In a like manner, the use of novel product A in certain specific applications or receiving media, or "products", is also novel. These applications employing product A or both product A and product B constitute further aspects of the present invention.

Figures 4, 5:
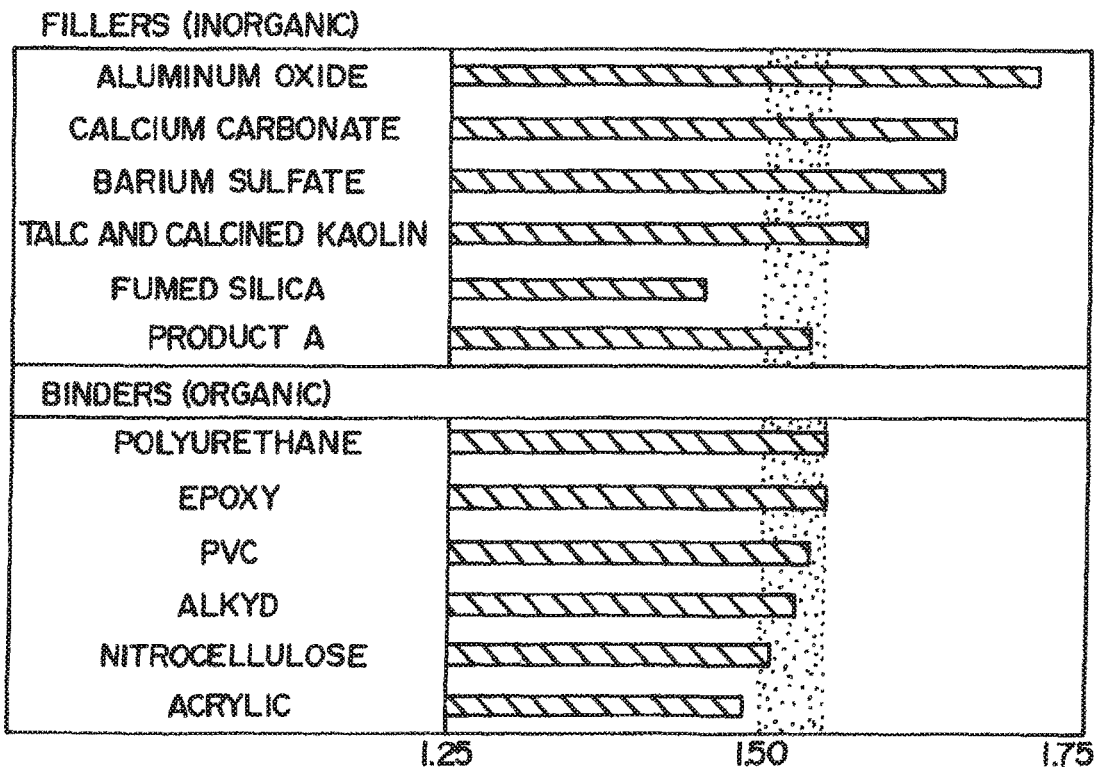
FIG. 4 is a table listing the mineral properties of the novel ultra fine nepheline syenite powder identified as product A.
FIG. 5 is a line graph of the average refractory index of mineral fillers and binder systems wherein the products of FIG. 2 and FIG. 3 are compared with other inorganic fillers and organic binders based upon refractory index, wherein the products of the present invention are illustrated by the vertical band highlighted on the graph.

The method shown in FIG. 1 is capable of making product A without the introduction of water and/or moisture that can cause agglomeration of the very fine powder necessary for the enhancement, advantages and properties associated with the present invention. When the particles are reduced from about 15 microns to less than 10 microns, and preferably less than 6 microns, moisture becomes a serious problem. It has been commercially impossible to produce nepheline syenite powder with a grain size of less than about 10 microns and, indeed, less than 6 microns without use of a wet process. FIG. 4 discloses specific properties of product A. The finer grain ultra fine nepheline syenite powder constituting product A is novel and is processed without water and has a brightness rating in the range of 90-93, a pH in the general range of 9-11, a grain size distribution of less than about 5 microns, and substantially free of particles less than about 0.2 microns. The distribution of the particle size in product A is in the general range of about 4-5 microns and the moisture content of both product A and product B is about 0.7%. Indeed, the moisture content of powder A is preferably less than 0.7%.

A commercial or final product or receiving media using the finer grain ultra fine nepheline syenite is loaded by a percentage of weight greater than about 6-10% in a receiving mixture. This type of product has a low refractory index of less than about 1.60. See FIG. 5. The mixture or media receiving product A as a filler or extender is essentially transparent to ultraviolet light; therefore, if the mixture or media is cured by ultraviolet light, product A will not affect the curing process. The end "product", i.e. the mixture receiving product A has a haze percentage of less than about 5-6% and a gloss control with a 60° gloss of less than 90. The product or mixture receiving product A has been found to have a pencil hardness that is improved 3-4 units and higher block resistance. The product or receiving mixture for product A is generally loaded in the range of 12-20% by weight; however, some products are loaded as low as 3-6% by weight.

Ultra fine nepheline syenite powder produced in accordance with the method of FIG. 1 has certain properties and is compared to existing particulate material for which product A is a replacement in FIGS. 5-13. Product A is compared in some drawings with product B to disclose where these powders obtain comparable results and where product A is superior to product B. Product A is a finer grain ultra fine nepheline syenite powder where the grain size is drastically reduced to a magnitude heretofore believed to be unobtainable in commercial quantities. Such small grains have a large reactive surface area and will agglomerate if exposed to moisture above 0.8% by weight as an end product or during production.

In FIG. 5 critical properties of various commercial fillers or binders are compared with product A used as an inorganic filler. The comparison uses the average refractive index of commercial mineral fillers and binder systems. As can be seen in the line graph, finer grain ultra fine nepheline syenite powder produced in accordance with the method of FIG. 1 has less refractive index than the common inorganic fillers. Aluminum oxide, calcium carbonate, barium sulfate and calcined kaolin adversely affect reflectivity to a greater extent than does finer grain ultra fine nepheline syenite powder. Only fumed silica in the inorganic filler group has a lesser average refractive index. Of course, use of silica is problematical due to certain environmental regulations. Thus, ultra fine nepheline syenite powder has a lesser refractive index than other commercial inorganic fillers. Indeed, product A has an average refractive index normally experienced by organic binders, which binders are more expensive. They result in less enhancement of those properties that are enhanced by use of product A. Thus, ultra fine nepheline syenite powder has a relatively low average refractive index which is an advantage in coatings.

Figure 6:
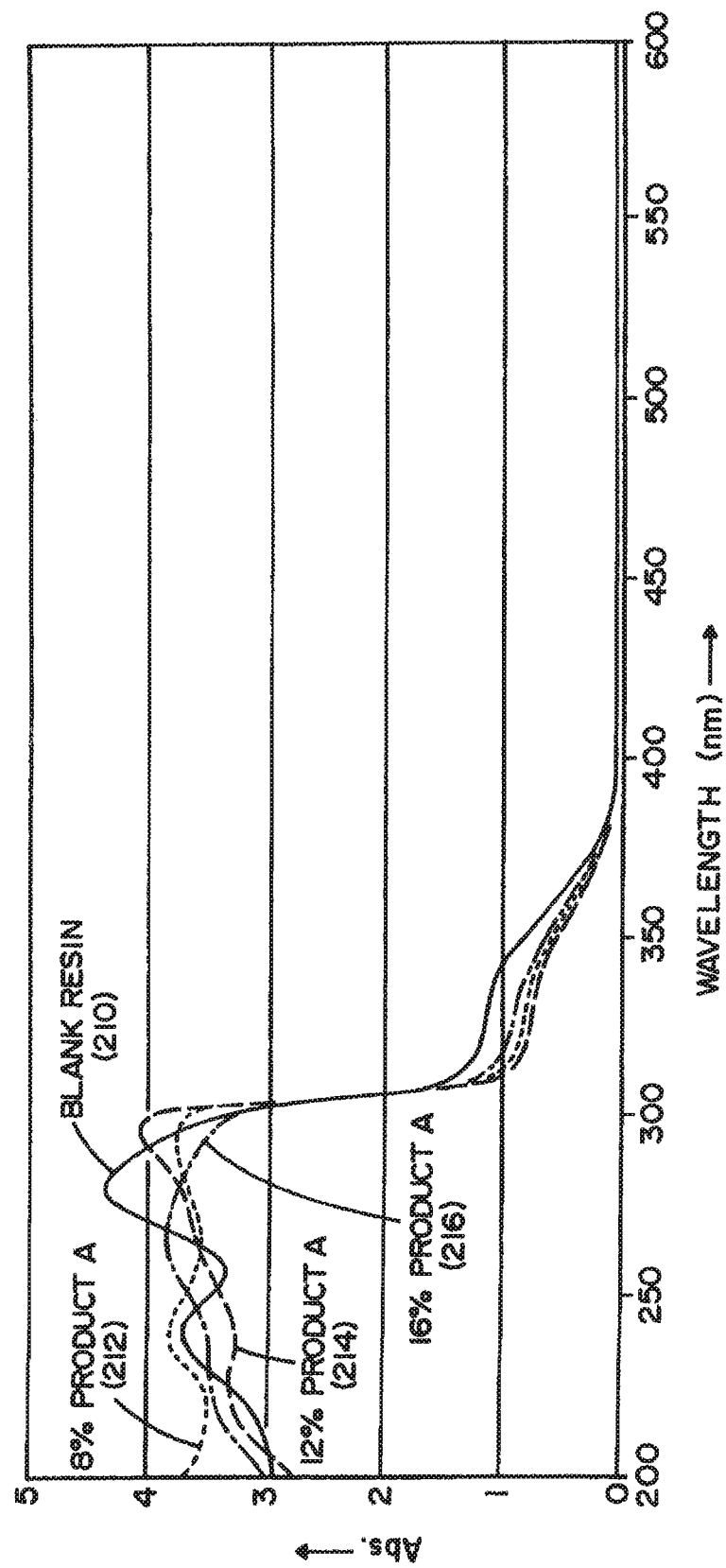
FIG. 6 is a chart illustrating the effect of loading for product A in a UV curable urethane coating, as it relates to the ability to cure the coating upon exposure to ultraviolet light.

The graph in FIG. 6 illustrates the effect of the level of loading of product A in the "product" or receiving media and how loading relates to the curability of an ultraviolet curable polyurethane coating. The UV absorptive characteristics of standard resin is shown by curve 210. Curve 212 represents the absorptive characteristics of a resin with 8% product A. In a like manner, the blocking characteristic for a resin with 12% product A is illustrated by curve 214. A resin having 16% product A creates a blocking characteristic illustrated as curve 216. This general level of transparency continues up to at least 20% loading of product A in the ultraviolet curable polyurethane resin. In summary, product A which is the finer grain ultra fine grain nepheline syenite powder has little, if any, effect on the curability of any ultraviolet curable resin and in some cases improves this property. This is an advantage not obtained by other larger grain fillers and is quite important. Indeed, product A actually improves UV curing (depth and cure time) since coating filled with nepheline syenite powder absorbs less of the UV light in the curing range of less than 300 nm than an unfilled system.

Figure 7:
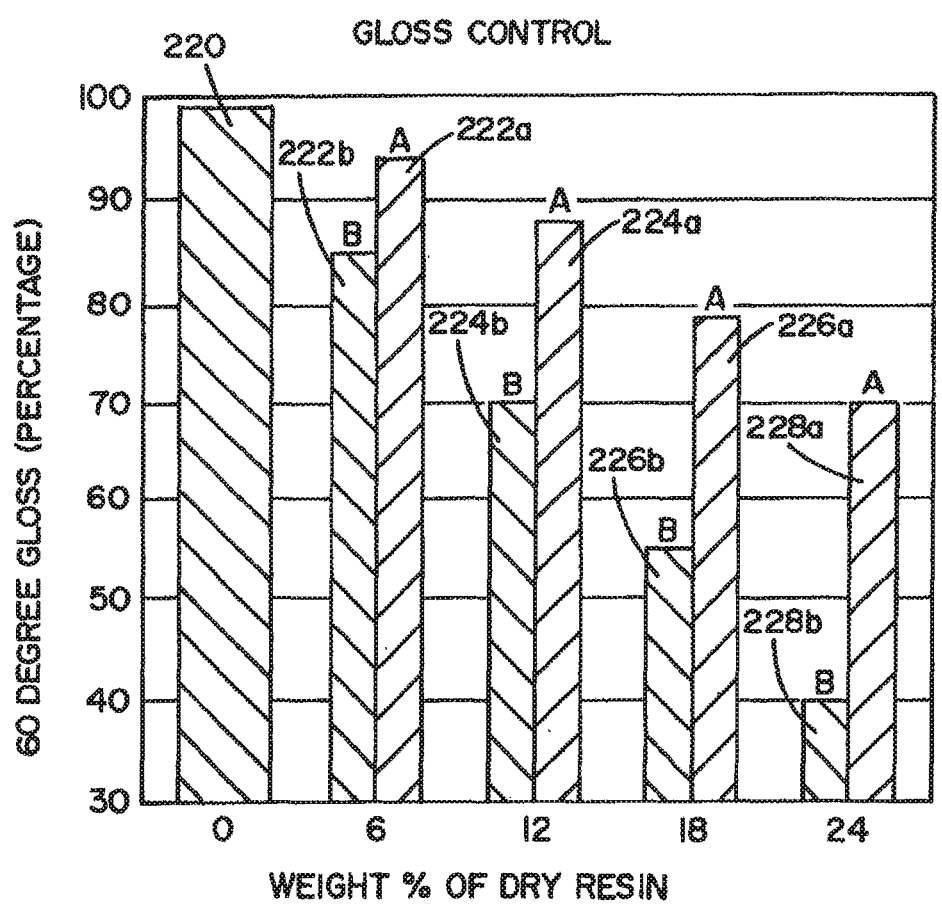
FIG. 7 is a vertical graph illustrating the gloss control capabilities of products A and B with respect to different loading in an aqueous ultraviolet polyurethane coating and a comparison of the coating gloss without the products being incorporated as a filler.
Figure 8:
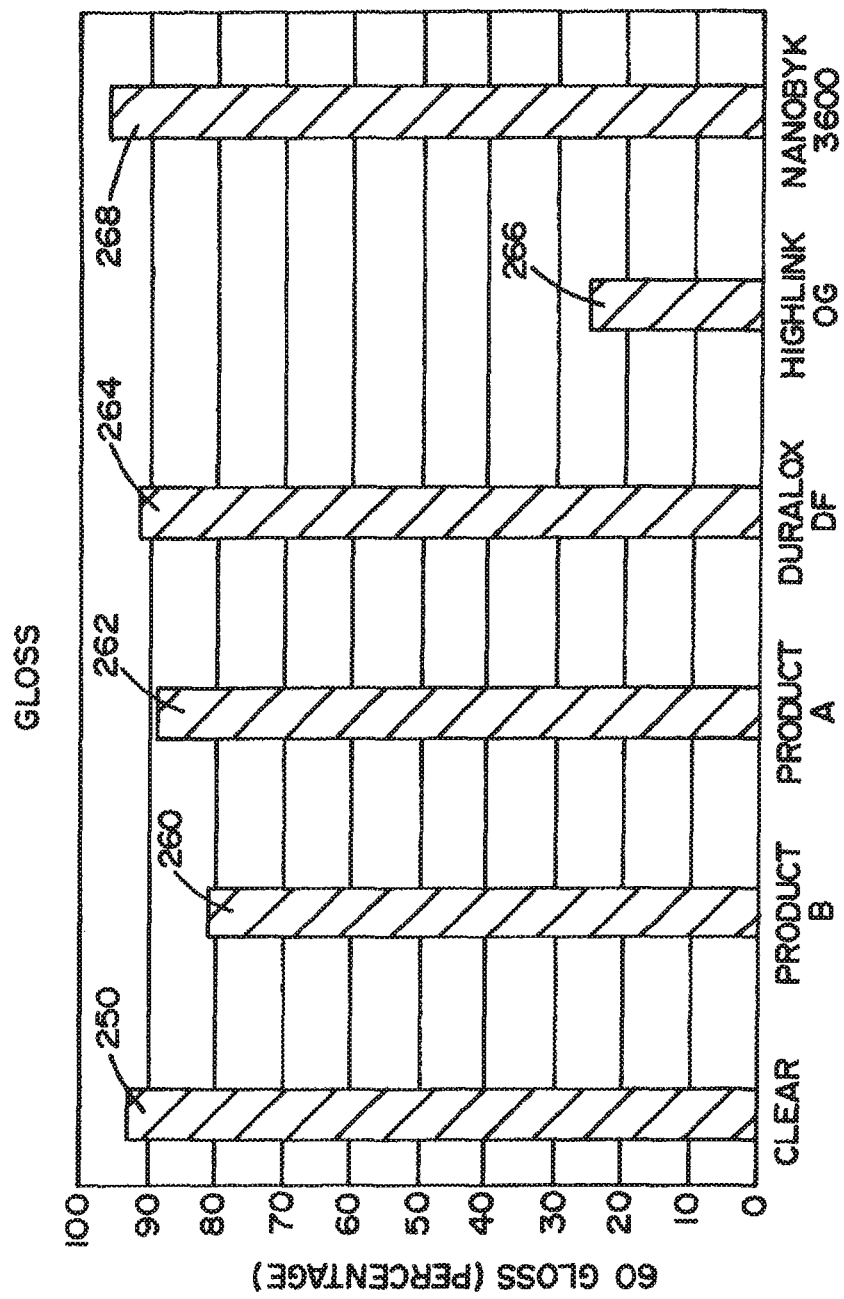
FIG. 8 is a vertical graph of the gloss obtained when using various fillers or binders in an aqueous ultraviolet cured PUD urethane coating as compared with a clear coating.

The use of ultra fine nepheline syenite powder is very effective for gloss control in aqueous ultraviolet acrylic coating. This feature is illustrated in the graph of FIG. 7. The data reveals that product A has less effect on gloss, than does product B. Without addition of products A or B, the gloss control is approximately 100% as indicated by vertical bar 220. By loading the coating with 6%, 12%, 18% and 24% ultra fine nepheline syenite powder, excellent gloss control is obtained. With 6% loading, gloss control for the products A and B is shown as vertical bars 222a, 222b. With 12% loading, the results shown by bars 224a, 224b are obtained. 18% loading results in values shown by bars 226a, 226b. 24% loading obtains the results shown by bars 228a and 228b. Thus, the loading and size of the ultra fine nepheline syenite is used to control gloss of a coating. The relationship of the gloss control obtained by products A and B, as compared to other common commercial fillers for ultraviolet cured coatings, is illustrated in the vertical graph in FIG. 8 which corresponds to information illustrated by the vertical graph in FIG. 7. Without any filler, the gloss percentage of a clear curable coating is over 90%, as shown by bar 250. When using product B, the gloss control value is illustrated by bar 260. Bar 262 represents the resulting gloss control obtainable by product A. FIGS. 7 and 8 show not only similarities between products A and B, but also the distinct superiority of product A in this area. Indeed, product A obtains a gloss control generally commensurate with a clear ultraviolet cured coating. Such high gloss control is obtained by Duralox DF, as shown by bar 264. This filler is highly expensive; however, it can be replaced by the relatively inexpensive product A, thereby gaining all the other advantages of product A without sacrificing clarity. Highlink OG, as shown by bar 266, has very little gloss control. High gloss control can be obtained by a nano product, such as Nanobyk 3600 as shown by bar 268. This commercial nano particle filler is quite expensive and has loading limits. It can be replaced by product A without losing much in gloss control while obtaining other advantages explained both earlier and hereafter. Thus, FIGS. 7 and 8 illustrate that finer grain ultra fine nepheline syenite (product A) has excellent gloss control characteristics and can be used as a substitute for expensive commercial fillers. However, the better gloss control of a coating is obtained by the lower percentage of loading such as loading of about 10-12% as disclosed in FIG. 7. Thus, product A has distinctly better gloss control ability than product B.

Figure 9:
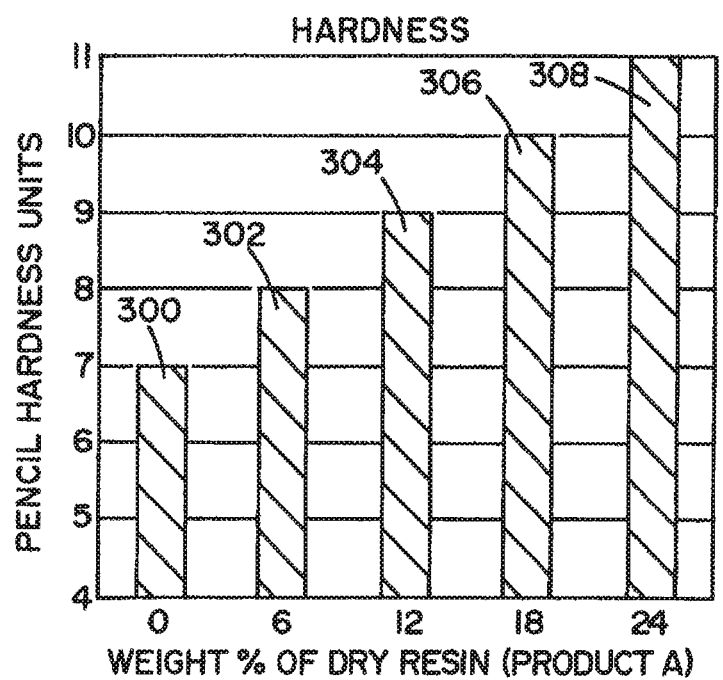
FIG. 9 is a vertical graph showing the pencil hardness of an aqueous ultraviolet polyurethane coating with different loadings of the novel product A illustrating that as the loading increases the hardness also increases.
Figure 10:
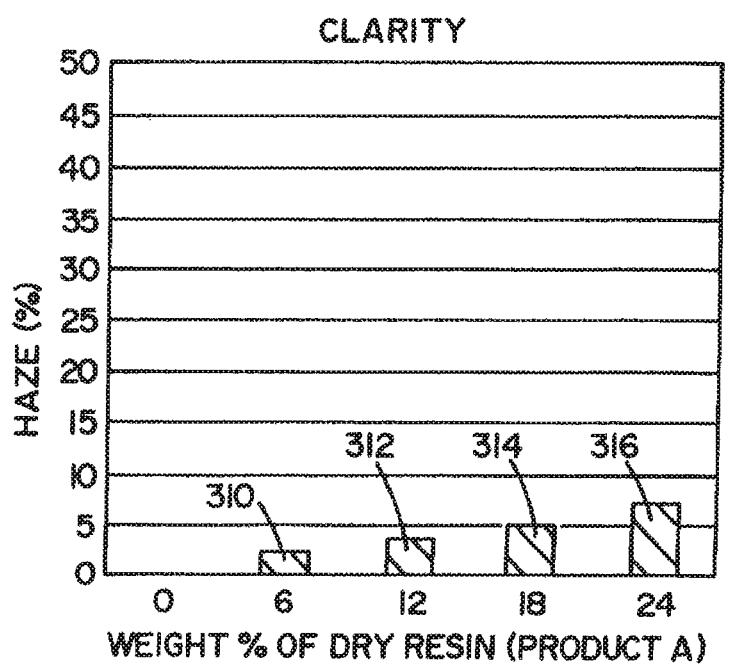
FIG. 10 is another vertical graph, similar to FIG. 9, illustrating the effect on coating clarity in the same coating for different loadings of product A. This graph shows that the addition of product A in an aqueous ultraviolet acrylic coating has minimal effect on the actual clarity of the resulting coating.
Figure 11:
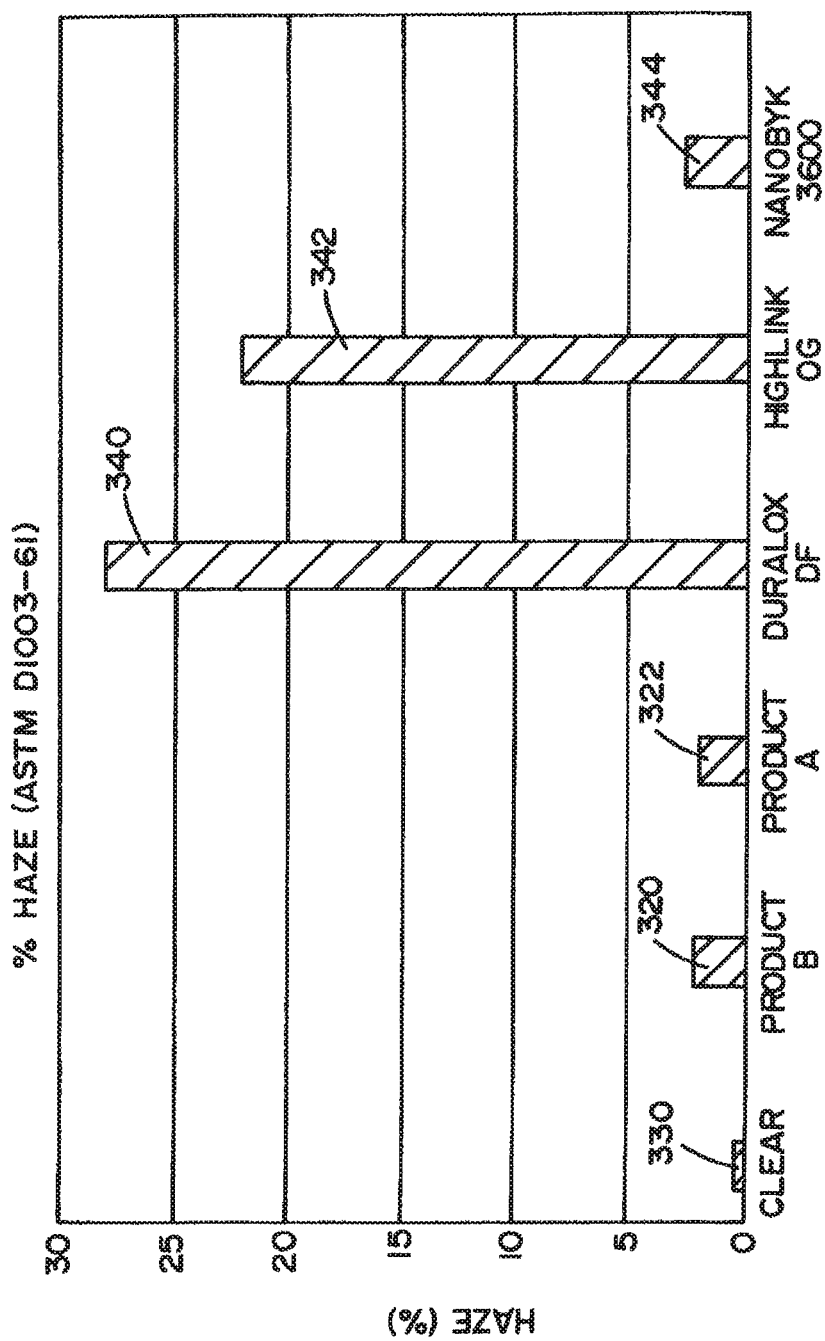
FIG. 11 is a vertical graph illustrating the percentage of haze (ASTM D1003-61) for the various fillers or binders illustrated in FIG. 8 and for the same coating as used in generating the graph of FIG. 8. This graph again illustrates that the addition of product A has a minimal effect on clarity and has a substantially lesser effect on haze than other competitive fillers or binders in urethane coatings and, indeed, in other coatings.

Another property of the finer grain ultra fine nepheline syenite powder, such as product A, is illustrated by the data represented in the graph of FIG. 9 showing units of increased pencil hardness. The loading of product A is shown to have a direct correlation to the number of pencil hardness unit for a coating such as an aqueous ultraviolet acrylic coating. Vertical bars 300, 302, 304, 306 and 308 show the increased pencil hardness units caused by increased loading of product A into a UV coating. Increased loading of product A increases the units of hardness of the receiving coating. The increased loading of product A has a minor effect on clarity, as shown in FIG. 10. As the percentage loading increases from 6% to 24%, the quality of the coating used to produce the data displayed in the graph of FIG. 9 is not affected, to any material extent, as indicated by heights of bars 310, 312, 314 and 316. Thus, the addition of product A does not significantly affect the clarity, but does substantially increase the units of pencil hardness of a coating. The minor effect on clarity with high loading is drastically less than normal fillers now used in ultraviolet coating, as shown in FIG. 11. The clarity values of products B and A are shown by bars 320, 322, respectively. Ultra fine nepheline syenite powder produced in accordance with the method of FIG. 1 has little effect on the clarity of the clear coating as represented by bar 330. However, a standard filler used in ultraviolet cured coating is Duralox DF. This filler has quite a large effect on clarity. This adverse effect is illustrated by the great height of vertical bar 340. In a like manner, another common filler which is Highlink OG has a substantial effect upon the clarity of the coating as represented by the height of bar 342. Consequently, both novel product A and existing product B have a minimal effect upon clarity, while other commercial fillers have the drastic effect upon clarity of the coating. To obtain the low effect on clarity using commercially available fillers, it is necessary to use a nano particle filler such as Nanobyk 2600 generating the clarity effect illustrated by the height of bar 344. As is well known, the use of nano particles in ultraviolet curable coatings is extremely expensive, which expense can be avoided by using the low cost mineral constituting product A. Thus, novel product A has a lower effect on clarity and increases the hardness of a coating. This combination of properties is not obtainable by other, non nepheline syenite commercial fillers for ultraviolet cured coatings and other coatings. This is a substantial advantage of finer grain ultra fine nepheline syenite powder and particularly at the higher loading levels allowed by product A. In summary, product A can be loaded to increase the hardness of the coating while not affecting the clarity of the coating. This advantage is obtained at a low cost with a mineral based product. Product A drastically reduces wear on equipment mixing the coating and is a substantial improvement over existing product B. Product A has a substantially lower Einlehner Abrasive Value than that obtained by product B.

Figure 12:
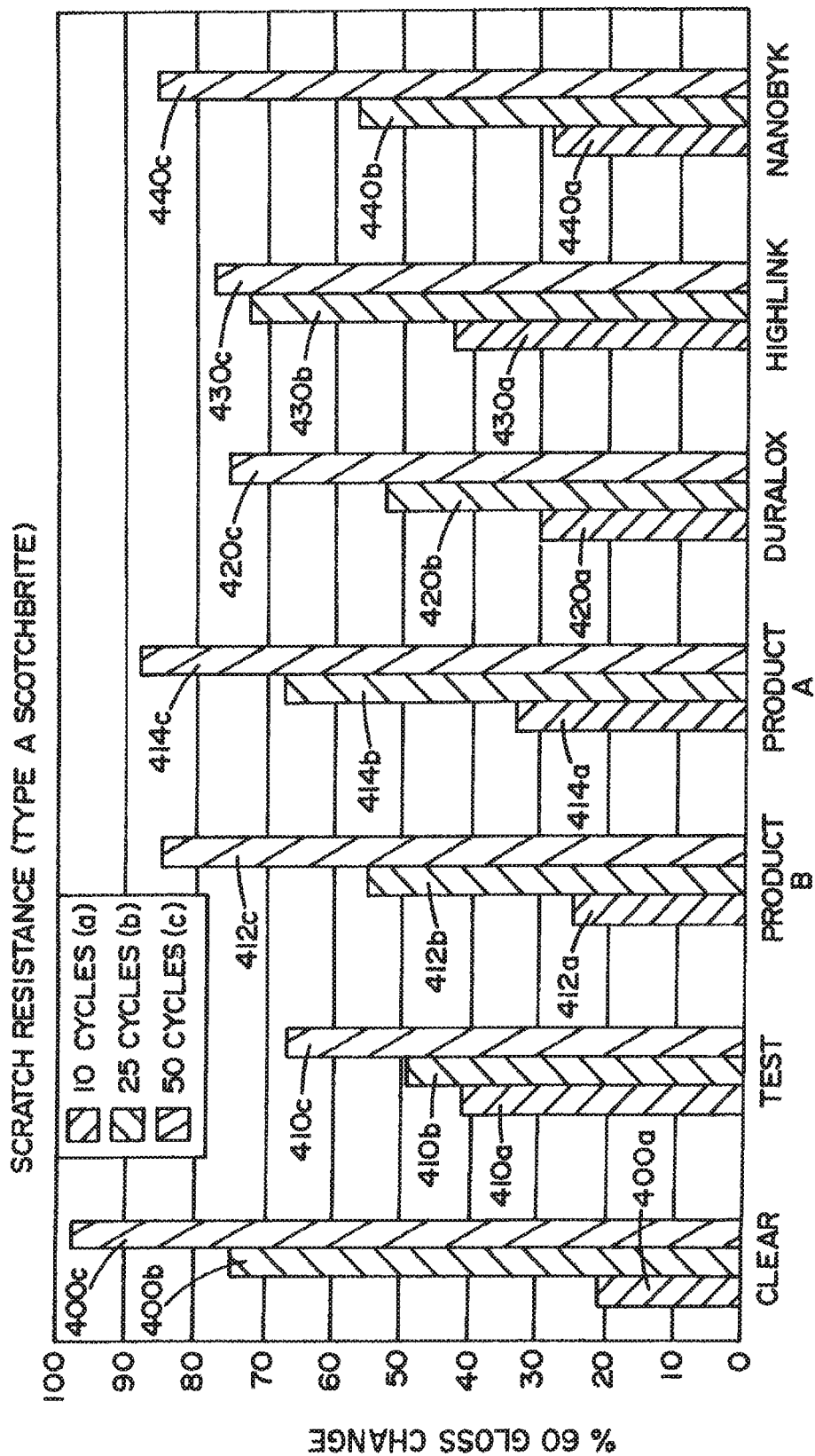
FIG. 12 is a vertical graph for the same coating as shown in FIG. 11 illustrating the scratch resistance (type A scotch-brite) obtainable by use of various commercial binders and the two ultra fine nepheline syenite powders (Products A and B). This graph illustrates that the coarser product has an advantage for aggressive scratch tests; however, the lesser grain size of the ultra fine nepheline syenite is more suitable for increasing film hardness.

Ultra fine nepheline syenite powder produces the advantages so far described and other physical advantages when used in a coating. These advantages are illustrated by the data presented in the graphs of FIGS. 12 and 13. These graphs relate to scratch resistance and block resistance, respectively, of a coating. The graph of FIG. 12 illustrates scratch resistance as compared to a clear ultraviolet coating. The clear coating results in the percentage gloss change for 10 cycles, 25 cycles and 50 cycles as illustrated by bars 400a, 400b, 400c, respectively. In a like manner, the larger grain ground nepheline syenite results in a gloss change as shown in bars 410a, 410b and 410c. Product B produces a gloss change for the various scratching cycles as illustrated by the heights of bars 412a, 412b and 412c. Product A produces the gloss changes illustrated by the heights of bars 414a, 414b and 414c. Product A improves aggressive scratch over the unfilled resin and approaches the performance of more costly nano size fillers or unfilled resin. The "test" filler is a nepheline syenite powder with a grain size less than 30 microns and is actually the best Scotchbrite Abrasion test resistance. Thus, the finer grain product A is more suitable for increased film hardness in the upper or outer portion or layer of the coating. Product A is superior to other common fillers, such as Durolox producing the scratch resistance results shown by bars 420a, 420b and 420c or Highlink producing the scratch resistance results shown by bars 430a, 430b and 430c. The only product that obtains comparable scratch resistance to the ultra fine nepheline syenite powder is the nano particle sold as Nanobyk having the results illustrated by bars 440a, 440b and 440c. Consequently, product A has a superior scratch resistance and produces a high hardness for the outer portion of the coating in which the powder is used.

Figure 13:
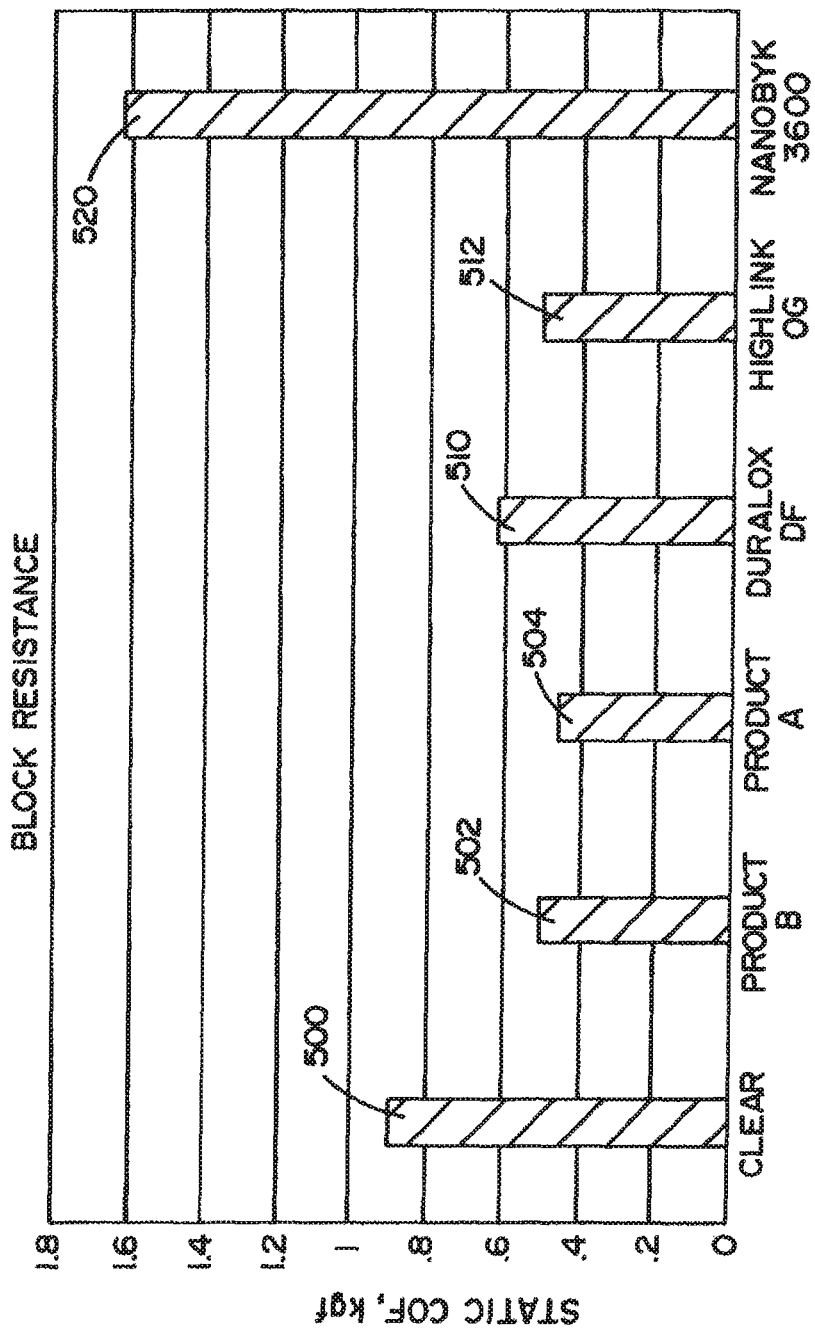
FIG. 13 is a vertical graph of the coating as illustrated in FIGS. 8, 11 and 12 revealing that the use of ultra fine nepheline syenite improves block resistance in the coating.

Block resistance comparisons for product A with the products of FIG. 12 are illustrated by the data shown in the graph of FIG. 13. The block resistance of a clear coating is represented by the static COF, $k_gf$ values represented by bar 500. Products B and A produce superior block resistance results as illustrated by bars 502 and 504, respectively. Block resistance for Durolox is represented by bar 510 which is lower or poorer than the resistance of either product A or product B. The same is true of the block resistance for Highlink OG, as shown by bar 512. More importantly, the nano particle filler sold as Nanobyk 3600 has a relatively low block resistance shown by bar 520. Consequently, even though the extremely expensive nano particle filler has certain advantageous characteristics that can be obtained by the relatively inexpensive product A, this nano particle product has a substantial negative effect on block resistance of the coating. Thus, product A is less expensive than the nano particle filler and has an enhanced block resistance characteristic which constitutes a drastic improvement over the nano particle filler.

For finer grain nepheline syenite powder, it has been found that the Einlehner Abrasive Value (EAV) is less than 100 for a maximum grain size of 10 microns and a value of about 50 for the preferred embodiment wherein the material has a maximum grain size of 6 microns. At 10 microns, the EAV or abrasion number is less than 100. Tests have indicated that the lower the EAV or abrasion number, the less wear there is on equipment processing viscous material using nepheline syenite powder. It is desirable to have a value less than 100 and preferably below 50. Product B has an EAV of substantially over 100 and, this fact was one of the motivations to seek a powder with less process wear characteristic. This very low abrasion value is obtained by novel product A wherein the grain size of the nepheline syenite powder is less than 6 microns and generally in the range of 1-6 microns. This is a very small range for the distribution profile and also is an ultra fine grain size. Product A is an improved nepheline syenite powder with capabilities heretofore not obtained economically in commercial quantities. The powder has the advantageous properties and characteristics herein disclosed together with the basic properties for which it was created.

In summary, FIGS. 5-13 are disclosed data representative of characteristics obtainable by novel product A. The properties of product A as illustrated in the graphs and disclosed in the written description of the present invention constitute advances in the coating technology. These results relating to the ultra fine nepheline syenite and disclosed properties of the existing product B have led to many novel applications of the ultra fine nepheline syenite powder identified as product A, as well as novel applications of product A itself.

Product A Summarized

In accordance with the first aspect of the present invention, finer grain ultra fine nepheline syenite powder is created having a grain size of less than 10 microns; however, product A as disclosed herein is an even finer grain nepheline syenite powder having a grain size less than about 6 microns. Consequently, the broad aspect of the invention is a nepheline syenite powder having a grain size demonstratively smaller than the grain size of product B, but in practice greatly less than the grain size of product B. It has been determined that a nepheline syenite powder having a grain size less than 10 microns produces an Einlehner Abrasive Value of less than 100. Thus, the powder drastically reduces the wear on equipment processing a compound using the new nepheline syenite powder. Product A has an Einlehner Abrasive Value of less than about 50. Product A has a moisture content of less than 0.8% and preferably about 0.7% so that the fineness of the grain size and, thus, the drastically increased reactive surface area does not cause agglomeration of the grains to defeat the beneficial properties of product A. Consequently, novel product A has a low moisture content less than about 0.8% that produces an Einlehner Abrasive Value of about 50. Such nepheline syenite powder has not been heretofore available for use where nepheline syenite is a preferred extender, filler or binder. Furthermore, when product A was created with a low moisture content and, a low abrasive value, it was found that this nepheline syenite powder can be used, not only where nepheline syenite powder or ground nepheline syenite has been used before, but also in other compounds that use commercial fine grain fillers or extenders, other than the mineral nepheline syenite. Product A has little if any free silica so the difficulties of handling and incorporating silica are avoided. Product A is a source of sodium and aluminum where sodium and aluminum are constituents necessary in the end product. In the preferred embodiment product A has constituents as listed below:

| | |
|---|---|
| Silicon dioxide | about 50-60% by weight |
| Aluminum oxide | about 20-25% by weight |
| Sodium oxide | about 5-10% by weight |
| Potassium oxide | about 5-10% by weigh |

By having aluminum oxide and sodium oxide the nepheline syenite powder of product A is an excellent source of sodium and aluminum and has silicon dioxide, but not free silica. Free silica in product A, if it exists at all, is less than 0.1%. Consequently, it is useful in compositions that require silicon dioxide, but not free silica, such as coatings, adhesives, sealants and inks. The drastically reduced grain size of product A causes easy dispersion in resin systems, allows use in coatings that have thin application levels, such as less than 10 microns, and produces low oil absorption in the ultimate compound. Since the fine grains of product A have a drastically increased surface area the mineral powder has a greatly enhanced natural surface wetting capability and allows high loading of over 10% by weight and optimally greater than 12% by weight. This mineral powder is extremely beneficial due to its small grain size in clear, ultraviolet, 100% solids and powder coatings. It has a high brightness, high abrasive resistance, high clarity, high gloss, high hardness and high stability. These factors make product A a drastic improvement over other powders, such as product B. Reduction in grain size has a logarithmic type relationship when creating certain characteristics. Consequently, there is not a linear enhancement of capabilities based upon the difference in grain size. Product A is a substitute for costly nano fillers and does not screen out ultraviolet radiation to prevent or reduce the curing effect in ultraviolet cured coatings. Thus, product A produces sodium, aluminum and silicon dioxide without significant free silica with its resulting environmental disadvantages. This summary defines the general characteristics of product A, which mineral powder is a first inventive aspect. Other features of product A have been previously described and may or may not be described again. Product A has been used in producing various products such as coatings, sealants, adhesives, inks, together with being useable in the manufacture of such products as glass, ceramic and glaze, plastics, and rubber components. Certain of these applications of the unique, novel product A have been developed and are hereinafter described.

Aqueous UV Cured Coating

The fine grain ultra fine nepheline syenite powder constituting product A was mixed into a water based UV cured formulation based upon Bayhydrol UV. Nepheline syenite powder with a grain size of less than 6 microns was loaded into the clear coating at different percentages to produce samples with 6% by weight, 12% by weight, 18% by weight and 24% by weight. To produce these samples, 100 parts Bayhydrol UV is mixed with 1.5 parts Irgacure 500 as a curing agent and mixed for twenty minutes. Thereafter, one part of Acrysol RM 825 is added to the clear coating and mixed well so product A can be sifted into the mixture as the mixture is being stirred. The first sample has 6% by weight of clear solids, the second sample has 12% by weight of clear solids, the third sample has 18% by weight of clear solids and the fourth sample has 24% by weight of clear solids. Thus, loading of 6-24% is represented by the four samples. The composition containing clear UV cured coating receives nepheline syenite powder with a grain size of less than 6 microns. This composition is mixed for 50 minutes using a hock blade operated at high speed of approximately 2200 rpm. The elevated grind of this composition forming the four samples is let down with about 25 parts of water and a small amount of BYK 346. The samples are each mixed for ten minutes at approximately 800 rpm and filtered through a 150 mesh screen. The mixture is slightly basic with a pH in the general range of 7.2 to 7.5. The viscosity of the four coating samples is in the range of 300 to 400 cps at 100 rpm. The viscosity and pH are the result of mixing the distinct percentages of product A with the water based UV cured coating. Each of the four samples was evaluated for gloss and clarity by being freshly stirred for a minimum of ten minutes. The sample was then applied to a Leneta chart, Form 2A with a 30 RDS rod. Each sample was allowed to dry at atmosphere condition for ten minutes followed by force drying at 49° C. for ten minutes. The samples were then exposed to three passes through an American Ultraviolet UV reactor equipped with a minimum pressure mercury lamp housed in an elliptical reflector. The lamp wattage was set at 300 WPI and the belt speed was approximately 25 FPM. The cure energy per pass was measured at 330 mj/cm$^2$ and 0.674 W/cm$^2$UVA. 25, 60 and 85 degrees was determined over the black portion of the chart with a BYK Gardner Tn-Gloss instrument. This represents a degree gloss. Clarity was determined over the black portion of the chart utilizing a BYK Gardner Color Guide with D65/10 lighting and geometry. Clarity is measured at Delta L relative to the black chart as standard. This is the procedure for measuring gloss and LAB clarity. To determine pencil hardness, the standard procedure was used. Again, each sample was freshly stirred for a minimum of 10 minutes and the samples were applied to plate glass with a 30 RDS rod. Each sample was allowed to air dry at an atmospheric condition for ten minutes, followed by force drying at 49° C. for ten minutes. The same curing process was used again for these samples. The surface MAR/scratch and gouge pencil hardness were determined after ASTM D3363. The pencil hardness units for the four specimens using the novel fine grain ultra fine nepheline syenite powder was measured. See data in FIG. 9. These results were compared to the pencil hardness units for samples processed in the same manner, but using grain sizes greater than 10 microns and also greater than 15 microns. It was found that only samples having nepheline syenite powder with a maximum grain size of 6 microns resulted in uniform increase in hardness units with concentration. Indeed, when the grain size was greater than 10 microns in other comparative samples produced in the same procedure and tested in the same manner, there was erratic and unpredictable behavior as sown in FIG. 26. Such behavior drastically limits the amount of nepheline syenite powder which can be incorporated into the ultraviolet curable coating. Only the use of ultra fine particles of less than 10 microns, indeed, less than about 6 microns has a uniform increase in hardness units with loading so that greater loading can be accomplished to enhance the operation of the coating and drastically reduce its cost.

For the purpose of determining optical clarity, the four specimens utilizing product A were freshly stirred for a minimum of 10 minutes and refiltered through 50 mesh silk. The samples were then applied to a cleaned 1×3 microscope slide with a 30 RDS rod. The samples were dried and cured with ultraviolet energy as previously described. Optical clarity was determined microscopically by an optical density technique. Reduction in optical clarity is determined by the percentage reduction in the gray scale value (or increase in white value) of a black standard at 100×. The result indicates that samples having different loadings of product A had a drastically reduced effect on optical clarity. See data in FIG. 10. Test samples having greater grain size nepheline syenite powder had substantial effect after the grain size exceeded a maximum size of 15 microns. The four specimens having loadings in the range of 6-24% by weight of clear solids had little effect on optical clarity, until 25% loading was used. This loading reduced slightly the optical clarity. On the other end, comparative specimens having a grain size substantially greater than 15 microns showed a drastic effect on clarity at as little as 15% loading. The same slides used for optical clarity evaluation were used for demonstrating the haze by ASTM D 1003-61. The haze of the films for the four samples having different loading of product A were compared with samples having the same loadings of nepheline syenite with a maximum grain size of 15 microns and greater. See data in FIG. 11. The haze was characterized by using a Cary 100 spectrophotometer equipped with a 73 mm diameter diffuse reflectance integrating sphere. A blank slide was used when obtaining the base line and scatter of the instrument. This test indicates that the products having nepheline syenite with a grain size of less than 6 microns has drastically less effect on the haze than nepheline syenite powder with a grain size substantially greater than 15 microns. See bar 330 in FIG. 11.

All of these tests indicate the substantial improvement of using nepheline syenite powder in an ultraviolet cured coating over nepheline syenite powder having greater grain size. These comparisons with larger particle size for nepheline syenite powder establishes the advantageous nature of drastically reducing the grain size for the powder, which reduced grain size not only results in these enhanced properties for the coating, but also drastically reduces the wear on the process equipment handling the coating, since the Einlehner Abrasive Value of the novel nepheline syenite powder is about 50. If the particle size is allowed to increase to about 10 microns, which is still less than the grain size of product B, there is still enhanced characteristics for the UV cured coating and the Einlehner Abrasive Value is less than 100. The drastically improved properties of UV cured coatings utilizing a nepheline syenite powder having a grain size less than 6 microns has been established by the four samples and their comparison with nepheline syenite powder having greater grain sizes. As a further advantage of using the finer grain ultra fine nepheline syenite powder, the pendulum hardness characteristics of the novel nepheline syenite powder was compared to such hardness of a product using a larger grain nepheline syenite powder. This property was determined using four samples with different loadings as previously described. The samples were mixed for at least 10 minutes at approximately 500 rpm and then drawn down randomly on 4×4 glass parts. The samples were also drawn down on metal test panels. All the drawn down samples were allowed to air flash at atmospheric conditions for approximately ten minutes and were forced dried at 49° C. for ten minutes. Then the coatings were cured. Pendulum hardness was then measured in accordance with standard techniques. It was established that the pendulum hardness for a coating using the ultra fine particles of product A was superior to the test samples utilizing larger particle sizes. Thus, the merits of the novel nepheline syenite powder has been well documented by many physical advantages over particle sizes of 15 microns and higher and other commercial fillers.

The four samples with the various loadings were then restirred for ten minutes and adjusted to 25% vehicle solids for spray application. This spray was used to develop test panels as follows:

Cherry veneer, sand 180 garnet, 220 garnet, blow
Spray B24P410A toner, dry
Spray B23P70 washcoat 1-4 butyl acetate, dry
Sand 320, wipe
Spray and wipe clean B23P54A wiping stain, dry
Lightly hi-lite, 00 steel wool, blow
Spray acid cure sealer, two coats, wet on dry and final cure
Sand, 240 stearated
Wipe and blow panels
Spray stirred topcoats (25 psi, air siphon gun)
Dry 10 min at 41 C, 14% RH. 100 L/min air movement
Dry 10 min at 49 C
Cure 3 passes, UV unit equipped with medium pressure mercury lamp, at 300 WPI, elliptical reflector, approx. 361 mj/cm2, 686 w/cm2 per pass Panels developed by the procedure outlined above using the four samples with the different amount of loading were then rated for clarity (See data in FIG. 10) and compared with panels utilizing tests samples including product B and a nepheline syenite powder with substantially greater grain size. Nepheline syenite powder tended to hide sand scratches; however, samples having no nepheline syenite had the best clarity. Samples having product A with 6% loading were about the same clarity as clear. In all instances, nepheline syenite powder having the ultra fine particles of less than 6 microns had substantially better clarity at the various loadings. Clarity for a given loading of product A was drastically better than clarity for nepheline syenite powder with a substantially greater grain size (see FIG. 10). It was found that nepheline syenite powder having a grain size of about 6 microns was substantially more clear than nepheline syenite powder having a grain size higher than 15 microns. In conclusion, it was indicated that the minerals evaluated for clarity utilizing the developed panels illustrated that nepheline syenite powder with a grain size less than 6 microns was the best, by far, with regard to optical clarity. As indicated before, a coating with product A has the least haze development, less resettling and a more uniform increase in the hardness with mineral loading. The clarity did decrease with mineral loading (See data in FIG. 10); however, a coating utilizing product A with a loading of between 12% and 18% by weight exhibited little if any decrease in the finish clarity. With grain size greater than 15-20 microns, it was quite problematic whether the optical clarity of the test samples was acceptable even at low loading. In conclusion, as the grain size of the powder increases over 15 microns, the nepheline syenite in the UV cured coating is questionable merely from a clarity standpoint. Thus, to obtain the advantages associated with the use of fine grain nepheline syenite powder without affecting clarity and having substantial loading for cost reduction, it is necessary to use product A as opposed to other nepheline syenite powders or other fillers as shown by the data in FIGS. 8, 11, 12 and 13.

By using the novel nepheline syenite powder in a water based UV cured formulation, it has been found that the novel powder can be loaded heavily into the coating without substantial effect on optical clarity. Thus, this type nepheline syenite powder having the best optical clarity also has the least haze development and least settlement due to its ultra fine grain size. Furthermore, there is a uniform increase in the hardness as it relates to the mineral loading in the coating. See data in graph of FIG. 9. Collected data indicates that between 12 and 18% product A in a coating, such as in an UV cured coating, is optimum. At this loading, the particles do not decrease clarity, but do accomplish the reduced cost and other enhanced characteristics of the ultra fine nepheline syenite powder. Loading between 10 and 18% produces a clear finish for a coating, such as UV top coating based upon Bayhydrol. With grain sizes greater than about 10 microns, the clarity is decreased rapidly with loading. Consequently, larger particle nepheline syenite powder can not be loaded heavily to get the benefits of low cost. Furthermore, higher grain material has a greater Einlehner Abrasive Value. The EAV is drastically over 100 for existing nepheline syenite powders so equipment processing the coating has a drastically reduced operational life and, thus, increase capital cost. When a coating with 18% product A is used there is less than 5% increase in haze and a 60° gloss decrease of only about 20 points. The hardness determination shows that this coating with an 18% loading results in similar hardness to a loading as high as 24%. Higher loadings do not drastically increase the hardness. Hardness is a linear property of loading. Smaller particle size gives erratic hardness and is, thus, less acceptable. All of these observations were made when testing four samples utilizing the different loading as previously described.

As indicated, nepheline syenite powder having a grain size of less than 6 microns produces the best optical clarity, the least haze development, least settling and the most uniform hardness development for nepheline syenite minerals used in aqueous UV coatings. As a result, it was concluded that utilizing 12-18% nepheline syenite having a grain size of less than 6% may be used with only a slight decrease in finished clarity. Thus, the fine grain ultra fine nepheline syenite powder has drastically enhanced physical characteristics over coatings utilizing larger grain size nepheline syenite powder. There is no area where use of nepheline syenite powder with a controlled grain size of less than 6% creates an adverse result over nepheline syenite powder in general. Consequently, the new powder has enhanced characteristics over existing nepheline syenite powder and no detrimental physical effect. These evaluations for aqueous UV cured coating have been shown to apply to all clear, UV cured, powdered and other wood coatings.

Other Wood Coatings

In the section above, product A was used to make certain samples of an aqueous UV cured formulation or compound based upon Bayhydrol UV. These samples were evaluated for clarity and performance properties as they related to other nepheline syenite powder used for the same coatings. This detailed presentation establishes that nepheline syenite powder with a grain size of less than 6 microns provided the best clarity in the coating chemistry with suggested loading levels approaching 18%. The larger grain nepheline syenite powder was unacceptable at levels greater than about 12% loading. Furthermore, with a maximum grain size of 6 microns, there was a drastic decrease in the resulting abrasive characteristics of the coating. With the novel powder, the abrasion reduction is essentially maximized at a low loading. See data in FIGS. 27 and 28. Thus, a coating using product A could be loaded to a higher amount thereby reducing the cost of the coating, without affecting clarity or abrasion resistance. The resultant drastic reduction in the wear of equipment processing and using the coating in the coating industry and excellent settling property were combined with lower cost. At the same time, vastly enhanced physical properties of product A were realized. To evaluate the advantages of a coating utilizing product A another analytical procedure was implemented. Seven different wood coating formulations including three solvent based coatings, three water based coatings, and one 100% solids UV coatings were formulated and tested for clarity, gloss and viscosity. The mineral loading was based upon the weight percent mineral on polymer or clear solids.

The three solvent based coatings were nitrocellulose lacquer, acrylic lacquer and acid cured varnish. Each of these coatings was produced with 12% loading of product A and 12% loading of product B for comparison. The samples of nitrocellulose lacquer, acrylic lacquer and acid cured varnish were then evaluated for gloss and clarity by applying the nitrocellulose and acrylic lacquers to a Leneta chart Form 7B with a 30 RDS rod. These samples were air flashed and then force dried at 49° C. The coating charts were allowed to set over night before they were evaluated. The acid cured varnish sample was applied to a Form 7B with a 15 RDS rod immediately after they were catalyzed. The samples were air flashed for 15 minutes and then force dried at 60° C. for 15 minutes. The coated charts for this third coating were also allowed to set overnight before they were evaluated. These samples were evaluated for gloss and LAB clarity. The samples of nitrocellulose lacquer and acrylic lacquer were also evaluated for optical clarity and haze after being processed by the procedure set forth in the previous section. The coatings were applied to a 1×3 inch microscope slide with the appropriate rod. Each slide used the same cure procedure as set forth above for these two coatings. Optical clarity was determined microscopically by an optical density technique. Reduction in optical clarity was determined as the percentage reduction in the gray scale value (or increase in white value) of a black standard at 100×. Haze was determined by ASTM D1003-61. The haze of the films was measured using a Cary 100 Cone. The clarity results of this evaluation showed that both product A and product B resulted in decreased clarity and gloss relative to non-mineral modified coatings. However, product A showed drastically improved clarity and less gloss reduction than product B for these three coatings. An acid cured varnish coating exhibited similar clarity and gloss reduction characteristics with product A coatings being superior to product B coatings.

The use of products A and B for the three aqueous coatings involved producing samples by developing a resin-free pigment paste consisting of product A and/or product B and a dispersant. After developing the resin-free pigment paste including product A and product B, these pastes were used for modifying the three different aqueous coating samples. The first coating in this group of samples was aqueous lacquer, which was based upon Rhoplex CL-204. This aqueous lacquer based upon an acrylic polymer was loaded with the nepheline syenite powder combined with Disperbyk 190 to produce the aforementioned resin-free pigment paste. The percentage of nepheline syenite powder was adjusted to a 12% loading to produce the final aqueous lacquer. Thus, the aqueous lacquer sample is formulated to have 12% nepheline syenite based on polymer solids of the coating. The aqueous lacquer samples were applied to a Form 7B with a 15 RDSD rod. The samples were flashed for 30 minutes and then force dried for 30 minutes at 49° C. Again, the coated charts were allowed to set overnight before they were evaluated. The second aqueous coating was a clear aqueous 2K acrylic formulation based upon Roshield 3257 and Bayhydur 302. The same resin-free pigment paste containing nepheline syenite powder as described before was added to the aqueous 2K acrylic formulation along with cross linking. The comparative 2K aqueous clear acrylic urethane formulation was also modified by Disperbyk 190 to match the level brought in by the pigment paste in the respective formulations for comparative purposes. Thus, a sample using product A, a sample using product B and a sample using a test clear coating were formulated for analyzing this second aqueous wood coating.

The third aqueous coating used to evaluate the properties of product A was second 2K aqueous coating, i.e. 2K PUD urethane coating. The 2K PUD formulation was based upon Alberdingk U915 and Bayhydur VP LS 2336. These samples of this third aqueous coating involved the use of the same resin-free pigment paste applied to the aqueous 2K PUD formulation along with cross linking. The clear 2K aqueous PUD urethane formulation was also modified by Disperbyk 190 to match the level brought in by the pigment paste for comparative purposes. The three aqueous coatings of the samples described in this section were aqueous lacquer, aqueous 2K acrylic urethane, and aqueous 2K PUD urethane. All of these aqueous coatings were modified by including the resin-free paste formed, as indicated, with nepheline syenite powder having a grain size of less than 6 microns. For comparison, samples were used with clear coatings and coatings using the same resin-free paste with larger nepheline syenite powder. The two 2K samples were applied to a Form 7B with a 15 RDS rod. They were immediately applied after cross linking. They were air flashed for 30 minutes and then force dried 30 minutes at 39° C. They were also allowed to set for seven days before any measurements were made. These three coatings, the aqueous lacquer and the two 2K coatings, all used a paste containing nepheline syenite powder with a grain size of less than 6 microns. The samples resulted in the same beneficial clarity, gloss and haze characteristics as the three samples of solvent based coatings.

The third type aqueous coating using finer grain nepheline syenite powder and revealing improved clarity, gloss and viscosity was a 100% solid UV coating. This coating started with a standard 100% solids clear UV formulation including Laromer, Ebecryl, Sartomer, Irgacure and small amounts of other constituents. This standard clear UV coating was mixed with 12% by weight of product A and product B to produce samples for analysis. The 100% solids UV samples were applied to a Leneta Form N2A with a 5 RDS rod. The samples were then exposed to one pass through an American Ultraviolet UV reactor equipped with a medium pressure mercury lamp housed in an elliptical reactor. Coatings were cured with one pass through the unit at 13 FPM with a lamp set at 300 WPI. The measured cured energy was 0.666 J/cm2 and 0.724 W/cm2. The samples were allowed to set overnight before they were evaluated. Determination was made for 20, 60 and 85 gloss over the black portion of the chart with a BYK Gardner Tri-Gloss Reflectometer. LAB clarity was also determined over the black portion of the chart using a BYK Gardner Color Guide with 65/10 lighting and geometry. The clarity was measured by a standard procedure. These samples showed a distinctly greater clarity, gloss control and reduced haze for use of nepheline syenite powder with a grain size less than 6 microns.

The seven coatings (three solvent based, three water based and one 100% sold UV) were formulated and measured as reported herein. This process established the distinct and significant advantage of using a nepheline syenite powder having a particle size less than 6 microns. When using this nepheline syenite powder to drastically reduce the wear on processing equipment, it has been established that it is also far superior to use an ultra fine nepheline syenite powder having a larger grain size. Clarity is less affected for increased loading. So the cost can be reduced without sacrificing clarity or increasing haze. Samples using nepheline syenite powder in acid cured varnish and in a 100% solids UV formulation were less affected by the presence of a nepheline syenite powder. In the other five coatings formulated and analyzed as reported in this section, neither of the two ultra fine nepheline powders caused a rapid and dramatic gloss reduction compared to clear formulations. However, product A produces higher 60° gloss than product B when incorporated in a cellulose lacquer system, an acrylic coating, and a 2K PUD urethane system. The acid cure varnish sample produced the best clarity when it used product A as its filler. The next best coating system benefitting in this particular property by use of product A was the 100% solid UV coating system. In all the other coating samples the insertion of 12% product A reduces clarity when compared to the non-nepheline syenite modified sample as measured by delta L. In the 100% solid UV systems and in the aqueous lacquer, product A produces smaller delta L values to give more clear films than nepheline syenite powder having larger grain sizes. All the samples tested indicated that nepheline syenite powder with a maximum grain size of 6 microns did modify the visual clarity of the products, but these products were substantially clearer than coating samples using larger grain sized powder. This is a distinct advantage justifying use of product A; however, product B also was beneficial in those coatings which, heretofore never used any type of ultra fine nepheline syenite powder. The overall conclusion is that the addition of ultra fine nepheline syenite to the formulations resulted in only a slight reduction in film clarity relative to the non-modified samples. However, though both product A and product B did not adversely affect clarity and haze until loading was considered. Higher loading of product A results in substantially more clear film than use of product B with the same loading. Thus, product A can be loaded more with the reduction of costs without the same amount of reduction in clarity associated with larger particle sizes.

The coating system least impacted by adding nepheline syenite powder was the acid cured varnish. The 100% solid UV coating is the next coating with the least impact by incorporating nepheline syenite powder. All the other coating systems evaluated and reported in this section did experience some decreased optical clarity, but product A was superior to product B. As to haze, the product A was drastically less haze than produced by the addition of the same amount of product B. As to viscosity, the introduction of either product A or product B results in slightly lower viscosity of the formulation. Introduction of nepheline syenite powder into the 100% solids UV formulation results in some increase in viscosity. Product A shows some slight thixotrophic behavior.

The nepheline syenite powder was added to the solvent based coatings by first making a concentrate in the form of pigment paste or dispersion from the novel nepheline syenite powder. The paste was added to the solvent based coating.

This was a satisfactory procedure for introducing nepheline syenite powder into solvent based coatings. The use of nepheline syenite powder in solvent based coatings is new, whether novel product A or existing product B. The use of resin-free pigment paste was employed for the aqueous based coatings. The use of any ultra fine nepheline syenite powder for such coatings is novel. As to the 100% solids UV coating, the nepheline syenite powder was added by direct mixing into the coating formulation. In these seven coatings analyzed in the process described in this section, it was new to use any type ultra fine nepheline syenite powder whether it be product A or product B. Consequently, the use of fine grain nepheline syenite powder in many instances is novel for specific coatings whereas the preferred nepheline syenite powder produces not only a novel coating, but also an improved novel coating. This analysis showed the advantage of using ultra fine nepheline syenite powder in these coatings and that, in most if not all instances, product A was more beneficial than product B.

Diverse Uses of Ultra Fine Nepheline Syenite Powder

After developing the novel use of ultra fine nepheline syenite powder for several wood coatings and other coatings, several other applications of ultra fine nepheline syenite powder have been discovered. These many new applications have been extremely successful and are commercially viable as new commercial products. These new products were developed after creation of the novel nepheline syenite powder with a grain size of less than 6 microns to drastically reduce wear on handling equipment and prevent rapid powder settlement. When the tremendous and unanticipated benefits of finer grain ultra fine nepheline syenite were discovered, these benefits motivated a vast area of research and development. The fruit of this endeavor was creation of these several new products. Indeed, this powder motivated project identified and developed new products that never used ultra fine nepheline syenite powder or, in some instances, never used nepheline syenite at all. Novelty in these products is not limited to the novel finer grain nepheline syenite powder, but also includes use of any ultra fine nepheline syenite powder.

The newly developed products using ultra fine nepheline syenite powder with loading of 3-20% by weight are tabulated and explained in Table I. This table identifies the new product using ultra fine nepheline syenite powder and the particulate material replaced by the nepheline syenite powder. In situations where the new product has never used an ultra fine nepheline syenite powder, the novelty involves the use of either product A or product B. This fact is listed in the last column of Table I. In instances where the novelty of a given product is the use of the novel nepheline syenite powder having a grain size of less than 6 microns, only product A is listed in the last column of the table. All these products have been formulated and found to provide at least the benefits identified in the third column of Table I. The listed benefits for each new product using an ultra fine nepheline syenite powder in general or fine grain ultra fine nepheline syenite powder in particular are given in the fourth column of Table I. The benefits are tabulated by numbers and identified at the end of Table I.

TABLE I

| Nepheline Syenite Use | Replacement For | Property Benefit* | Reason for Benefit | NS Product** |
|---|---|---|---|---|
| Clear liquid wood coatings (including air, bake, moisture, and UV cured, solvent and aqueous, low VOC, 100% solids) | Resin | 1, 2, 3, 9, 15, 16 | 1 - reduced unit cost; 2, 3 - mineral hardness; 9 - nepheline syenite imparts UV stability, 15 - increases formula volume solids, 16 - non-UV absorber | A and B |
| Clear liquid wood coatings (including air, bake, moisture, and UV cured, solvent and aqueous, low VOC, 100% solids) | Conventional mineral fillers (excluding nepheline syenite) | 2, 3, 4, 5, 8, 9, 10, 15, 16, 17 | 2, 3 - mineral hardness; 4, 5 - refractive index; 8 - particle size/Stoke's Law; 9 - nepheline syenite imparts UV stability; 10 - low oil absorption, 15 - increases formula volume solids, 16 - non-UV absorber, 17 - self dispersing due to surface chemistry | A and B |
| Clear liquid wood coatings (including air, bake, moisture, and UV cured, solvent and aqueous, low VOC, 100% solids) | Standard (non-ultra fine) nepheline syenite | 2, 3, 4, 6, 8 | 2, 3 - uniform distribution of hard particles; 4, 6, 8 - particle size | A and B |
| Clear liquid wood coatings (including air, bake, moisture, and UV cured, solvent and aqueous, low VOC, 100% solids) | Nano mineral fillers | 1, 9, 10, 11, 15, 16, 17 | 1 - reduced unit cost; 9 - nepheline syenite imparts UV stability; 10 - low oil absorption; 11 - favorable particle surface chemistry, 15 - increases formula volume solids, 16 - non-UV absorber, 17 - self dispersing due to surface chemistry | A and B |
| Clear liquid coatings for flexible substrates (paper, leather, overprint varnishes, etc.) | Same as all above | Same as all above | Same as all above | A and B |

TABLE I-continued

| Nepheline Syenite Use | Replacement For | Property Benefit* | Reason for Benefit | NS Product** |
|---|---|---|---|---|
| Clear liquid coatings for other rigid substrates (metal and coil, laminates, etc.) | Same as above | Same as above plus 18 for metallic coatings | Same as above; 18 - buffering due to high pH. | A and B |
| Opaque liquid coatings (architectural trade sales, industrial and OEM coatings) | Same as above | Same as above plus 19 when used in combination with other mineral fillers. | Same as above; 19 - optimized pigment spacing. | A |
| Thin (<10 micron) coatings | Same as all above | Same as all above plus 13 (except for nano fillers) | Same as all above; 13 - particle size | A |
| Nail Polish | Same as above | Same as above | Same as above | A and B |
| Inks | Resin | 1, 2, 3 | 1 - reduced unit cost; 2, 3 - mineral hardness | A |
| Powder Coatings | Resin | 1, 2, 3, 9 | 1 - reduced unit cost; 2, 3 - mineral hardness; 9 - nepheline syenite imparts UV stability | A |
| Powder Coatings | Conventional fillers (e.g. CaCO3, barite) | 2, 3, 4, 5, 8, 9, 12 | 2, 3 - mineral hardness; 4, 5 - refractive index; 8 - particle size/Stoke's Law; 9 - nepheline syenite imparts UV stability; 12 - lower filler bulk density | A |
| Powder Coatings | Standard (non-ultra fine) nepheline syenite | 2, 3, 4, 6 | 2, 3 - uniform distribution of hard particles; 4, 6 - particle size | A |
| Powder Coatings | Nano mineral fillers | 1, 9, 10, 11 | 1 - reduced unit cost; 9 - nepheline syenite imparts UV stability; 10 - low oil absorption; 11 - favorable particle surface chemistry | A |
| Ceramic Bodies and Glazes | Conventional minerals (feldspar, silica, kaolin) | 5, 7, 20 | 5 - refractive index; 7 - aluminum source; 20 - lower melt T and lack of silica | A |
| Ceramic Bodies and Glazes | Standard (non-ultra fine) nepheline syenite | 7 | Higher surface area | A |
| Glass | Conventional minerals (feldspar, silica) | 5, 7 | 5 - Refractive index; 7 - aluminum source | A and B |
| Glass | Standard (non-ultra fine) nepheline syenite | 7 | Higher surface area | A and B |
| Metallurgical Slags | Conventional minerals (feldspar, silica) | 7 | Aluminum source | A and B |
| Metallurgical Slags | Standard (non-ultra fine) nepheline syenite | 7 | Higher surface area | A and B |
| Refractory Filler | Standard (non-ultra fine) nepheline syenite | 3 | Uniform distribution of hard particles | A and B |

TABLE I-continued

| Nepheline Syenite Use | Replacement For | Property Benefit* | Reason for Benefit | NS Product** |
|---|---|---|---|---|
| Plastics and rubber fillers | Resin | 1 (depending on resin); 2, 3, 9, 14 | 1 - reduced unit cost; 2, 3 - mineral hardness; 9 - nepheline syenite imparts UV stability; 14 - resin dilution | A |
| Plastics and rubber fillers | Conventional fillers | 2, 3, 4, 9, 13 | 2, 3 - mineral hardness; 4 - refractive index; 9 - nepheline syenite imparts UV stability; 13 - particle size | A |
| Plastics and rubber fillers | Standard (non-ultrafine) nepheline syenite | 2, 3, 4, 6, 13 | 2, 3 - uniform distribution of hard particles; 4, 6, 13 - particle size | A |
| Plastics and rubber fillers | Nano fillers | 1, 9, 11 | 1 - reduced unit cost; 9 - nepheline syenite imparts UV stability; 11 - favorable particle surface chemistry | A |
| Color Concentrates | Pigment | 1 | 1 - reduced unit cost | A |
| Color Concentrates | Conventional fillers | 5 | 5 - refractive index | A |
| Pigment Pastes | Pigment | 1 | 1 - reduced unit cost | A and B |
| Pigment Pastes | Conventional fillers | 5 | 5 - refractive index | A and B |

*Property Benefits:
1. Reduced Cost
2. Improved Durability: Scratch/Scrub/Abrasion Resistance
3. Improved Hardness and Block Resistance (coatings); Improved mechanical properties (plastics and rubber, refractory filler)
4. Clarity/Haze/Gloss
5. Low Tint Strength
6. Reduced Process Equipment Wear
7. Aluminum Source/Reduces Melting Point of Other Minerals - Process Economics
8. Reduced Settling
9. Improved Tint Retention and UV Stability
10. Low Resin Demand
11. Ease of Formulation
12. Economical Coating Coverage
13. Reduced Surface Defects
14. Flame Retardancy
15. Reduced VOCs (Volatile Organic Compounds)
16. Improved Curing Efficiency (cure time and thickness)
17. Lower Formulation Viscosity
18. Reduced substrate corrosion
19. Enhanced pigment efficiency/opacity
20. Controlled and consistent thermal expansion properties.

Table I discloses a tremendous advancement in the art or industry of using processed material minerals. This technical advancement created a new group of goods and had its birth in unlikely development of ultra fine nepheline syenite powder having a grain size of less than 6 microns. When this new and novel powder was developed to reduce equipment wear and reduce settlement by dramatically reducing the grain size to a level heretofore believed unobtainable, especially at a cost allowing commercial use, it was discovered after much research that this new powder presented a technical difference in kind. The new powder had unforeseen advantages when used in many coatings and in other bulk compounds. Consequently, using this unique nepheline syenite powder, many heretofore unimaginable uses of nepheline syenite powder have been invented. These novel products use ultra fine nepheline syenite powder. It has been determined and discovered that some of these products have novelty based merely upon the fact that they use finer grain ultra fine nepheline syenite powder. i.e. powder with a grain size of less than about 6-10 microns. Nepheline syenite powder as a filler or additive was heretofore unknown, then the novelty is use of any ultra fine nepheline syenite powder, i.e. a grain size less than 15 microns. Consequently, the products disclosed in Table I are novel because (a) they use ultra fine nepheline syenite powder or (b) they are uniquely enhanced by use of the novel finer grain ultra fine nepheline syenite powder.

To determine the advantages and characteristics of the various products as enumerated in Table I, the following test methods and typical values were used.
1. Material Unit Cost and Concentration Calculations
2. Steel wool double rubs, measure change in 60 deg., gloss, results range from no change to 80 units change (Note: improvements noted even at low, e.g. less than 3%, concentrations.)
3. Pencil gouge hardness (ASTM D3363), results from 6 to 12 "pencil hardness units", data available, block resistance determined by static COF measurements, results from 0.2 to 1.5 kgf; for plastics and rubber, evaluations of tensile, tear and impact properties.
4. Haze, measured in percent, ASTM D-1003-61, results from 0 to 100%, data available; 60 degree gloss measured with BYK Gardner Tri-Gloss instrument, results from 20 to 100.
5. Tint strength determined by change in color values (L, a, b).
6. Indication of equipment wear given by Einlehner Abrasion Tester AT-1000, results from 0 to 550 depending on mineral hardness and top size.

7. Reduced flux/sintering/melting temperature.
8. Settling determined by visual inspection of coatings formulations, ASTM D869.
9. Tint Retention and UV stability determined by outdoor (e.g. Florida, ASTM D1006) and accelerated (e.g. QUV, ASTM D4587) exposures, followed by visual inspection.
10. Indication of resin demand provided by oil absorption method ASTM D281, results from 10 to 130.
11. Ease of formulation determined qualitatively using such factors as the mixing intensity and the need for dispersing additives to provide a uniform coatings system.
12. Weight of powder required to cover a given surface area at a given coatings thickness.
13. Visual inspection.
14. Volume solids calculations.
15. Standard VOC calculations.
16. Absorbance spectra in UV range (300-400 nm wavelength) of coatings mounted on UV-transparent fused silica discs.
17. Krebs Stormer viscosity (ASTM D562), Brookfield viscosity (ASTM D2196), and ICI cone and plate (ASTM D4287) viscosity determinations.
18. Salt fog exposures of coated metal panels; measure "creep" (i.e. widest point on X scribe line where metal is visible) length.
19. Opacity at a given pigment (e.g. TiO2) loading as determined by contrast ratio.
20. Dimensional measurements.

The ink developed and listed in Table I has a loading of as low as 3% of the novel finer grain nepheline syenite powder. Thus, its loading was between 3-20% by weight of nepheline syenite powder. Moisture content of the powder was drastically less than 0.8% by weight. Indeed, it was about 0.4-0.5%. In the preferred embodiment, the ink is selected from the class consisting of flexographic ink, overlay varnishes and UV-cured ink.

Another recently developed application of the ultra fine nepheline syenite powder with a grain size of less than about 6 microns is for cast urethane rolls used in apparatus where an ultra smooth and wear resistant outer surface is desirable long life and smooth non-stick operation. Such rolls are used in printers, copiers and other high technology printing or copying equipment. These rolls must have an ultra smooth outer surface; consequently, it has been found that a filler of an ultra fine nepheline syenite powder of the type identified as product A was extremely beneficial. Such powder causes a drastic increase in cast smoothness so there is no need for further surface smoothing Even use of a filler with a grain size as low as 15 microns causes unwanted surface irregularities. To make the rolls, the ultra fine nepheline syenite powder is first heated to drive out even a very low amount of moisture, in the area of 0.6-0.8% by weight. The moisture content is less than 0.2%. Small amounts of moisture cause blistering or trapped carbon dioxide in the surface of the urethane castings. By further removing moisture from the ultra fine nepheline syenite powder having a very reduced grain size, the powder is mixed into the urethane in protected equipment so no moisture can be attracted. Thereafter, the urethane rolls are cast. They have an ultra smooth outer surface dictated by the finer grain of the nepheline syenite powder having a grain size of less than 6 microns. These polymer castings constitute rolls that are another commercial unit that has been invented upon creation of product A.

In summary, invention of product A has created a vast array of diverse products that can be beneficially modified by use of the novel nepheline syenite powder and/or by use of ultra fine nepheline syenite powder in general.

Features and Some Discovered Benefits of Novel Powder

Nepheline syenite is a naturally occurring, silicon deficient, sodium-potassium alumina silicate. It has less than 0.1% crystalline and silica. Indeed, substantially no free crystalline silica is detectable in the mineral complex which is ground and then particulated into the novel powder of the present invention. Fillers or extenders produced by the nepheline syenite powder of the present invention is a performance enhancer in a broad range of coatings, adhesives, sealants and inks. Indeed, the new powder is used to provide a new cast roll and is used in components such as glass and ceramic parts. Excellent brightness, tint retention, and wheatherability are achieved by use of the novel powder in many exterior systems, such as coatings. Improved color, chemical and scratch resistance also results when the novel nepheline syenite powder is used in coating formulations. The novel nepheline syenite powder is easily dispersed and settled quite slowly in all conventional resin systems. The new powder sometimes acts like a colloidal in a viscous matrix. Its low oil absorption and natural surface wetting characteristics permit high loading, with low viscosity, in adhesives, sealants, and aqueous and solvent based coatings. The ultra fine nepheline syenite powder with a grain size of less than 6 microns is ideally suited for clear, UV and powder coating systems requiring high gloss and optimum clarity based on its unique particle size distribution and light transmission properties. When used for parts such as cast roll, glass parts and ceramic parts, the new powder prevents settling and reduces wear on process equipment.

A variety of different uses and applications of nepheline syenite powder were investigated. Various formulations comprising the nepheline syenite powder of the present invention, were prepared. A summary of the wide array of different uses of nepheline syenite and representative commercially available products known to use ultra fine nepheline syenite are set forth below in Table II. Improvements and benefits as described herein are attainable by use of the present invention nepheline syenite powder of the present invention.

TABLE II

| Nepheline Syenite Use | Final Product | Loading (wt % dry resin) |
| --- | --- | --- |
| Clear liquid wood coatings (including air, bake, moisture, and UV cured, solvent and aqueous, low VOC, 100% solids) | HDROPLUS, HD SYSTEMS THOMPSON'S WATER SEAL, SAMUEL CABOT, RED SPOT, MINWAX, WOOLMAN. | 3-25% |

TABLE II-continued

| Nepheline Syenite Use | Final Product | Loading (wt % dry resin) |
|---|---|---|
| Clear liquid coatings for flexible substrates (paper, leather, overprint varnishes, etc.) | DYNACOAT UV | 3-20% |
| Clear liquid coatings for other rigid substrates (metal and coil, laminates, etc.) | WEATHERX | 3-25% |
| Opaque liquid coatings (architectural trade sales, industrial and OEM coatings) | BEHR PREMIUM PLUS, OLYMPIC, AMERICAN TRADITIONS, KILZ, DUTCHBOY, | 5-35% |
| Thin (<10 micron) coatings | WEATJERX | 3-20% |
| Nail Polish | REVLON | 3-20% |
| Inks | ARROWWEB, ARROWSTAR | 3-30% |
| Powder Coatings | POWDURA, ALESTA, DUPONT, INTERPON, ENVIROCRON, ROHM AND HAAS POWDER COATINGS | 5-25% |
| Ceramic Bodies and Glazes | Standard | 10-30% |
| Glass | ANDERSON, PPG | 5-20% |
| Metallurgical Slags | Ferrous Metals | at least 5% |
| Refractory Filler | Standard | 3-25% |
| Plastics and rubber fillers | Standard | 3-25% |
| Color Concentrates | Standard | 10-50% |
| Pigment Pastes | Standard | 10-50% |

Another non-limiting general composition of nepheline syenite is set forth below in weight percent:

| | |
|---|---|
| $SiO_2$ | 59-62 |
| $Al_2O_3$ | 22-24 |
| $Na_2O$ | 9-12 |
| $K_2O$ | 4-6 |
| $Fe_2O_3$ | <0.2 |
| $CaO$ | <0.5 |
| $MgO$ | <0.1 |

Yet another embodiment of the novel nepheline syenite powder of the present invention has the following proposition:

| | |
|---|---|
| Silican Dioxide | 60.20% by weight |
| Aluminum Oxide | 23.60% by weight |
| Sodium Oxide | 10.50% by weight |
| Potassium Oxide | 4.80% by weight |
| Calcium Oxide | 0.35% by weight |
| Iron Oxide | 0.08% by weight |
| Magnesium Oxide | 0.02% by weight |

As set forth in this description, 10-20% of product A used in a coating creates a minimal increase in haze. Indeed, the increase is less than 6% and 18% loading of product A results in a gloss decrease of about 20 points relative to an unmodified coating. When using a larger grain nepheline syenite powder, there is a dramatic decrease in gloss as compared with use of a nepheline syenite powder having a grain size of less than 6 microns. The advantage of using nepheline syenite powder with a grain size of less than 6 microns is that the pencil hardness increase with concentration of the powder is consistent. See data reported in FIG. 26. This is not the case with larger grain sizes for nepheline syenite powder. It has been found that these advantages of ultra fine nepheline syenite powder are enhanced, by use of nepheline syenite powder having a grain size of less than 6 microns.

Figure 26:
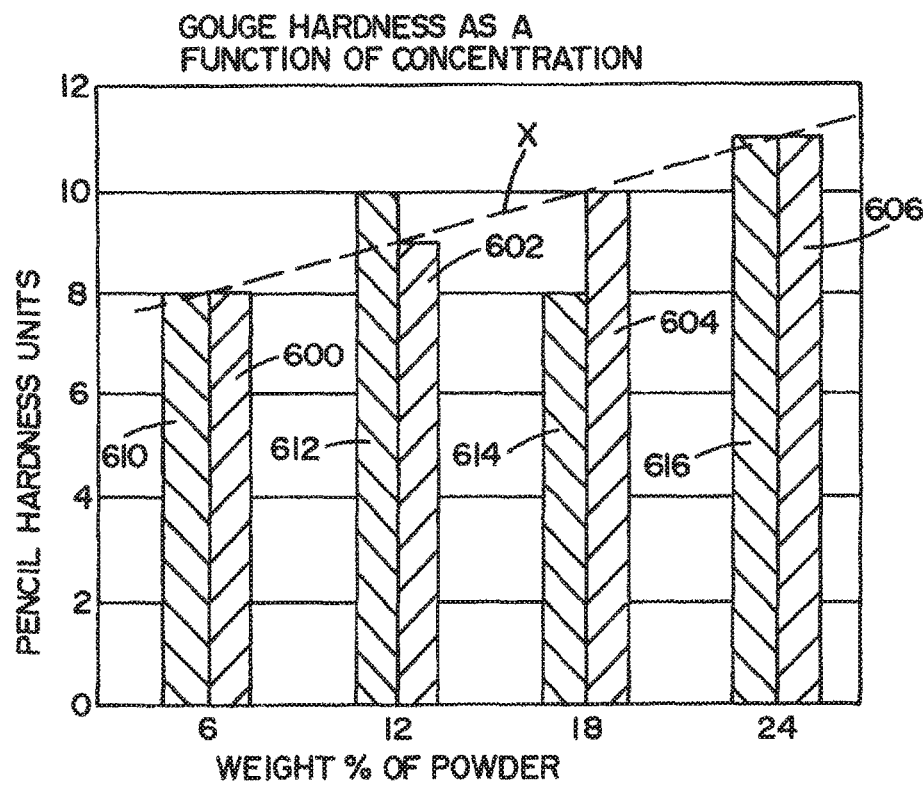
FIGS. 26 and 27 are a bar or vertical graph and a pictorial view, respectively, showing a hardness property and an associated scrub property of the novel nepheline syenite powder used in a polyurethane coating; and, FIG. 28 is a vertical graph showing change in gloss for product A and product B at different loadings.
Figure 27:
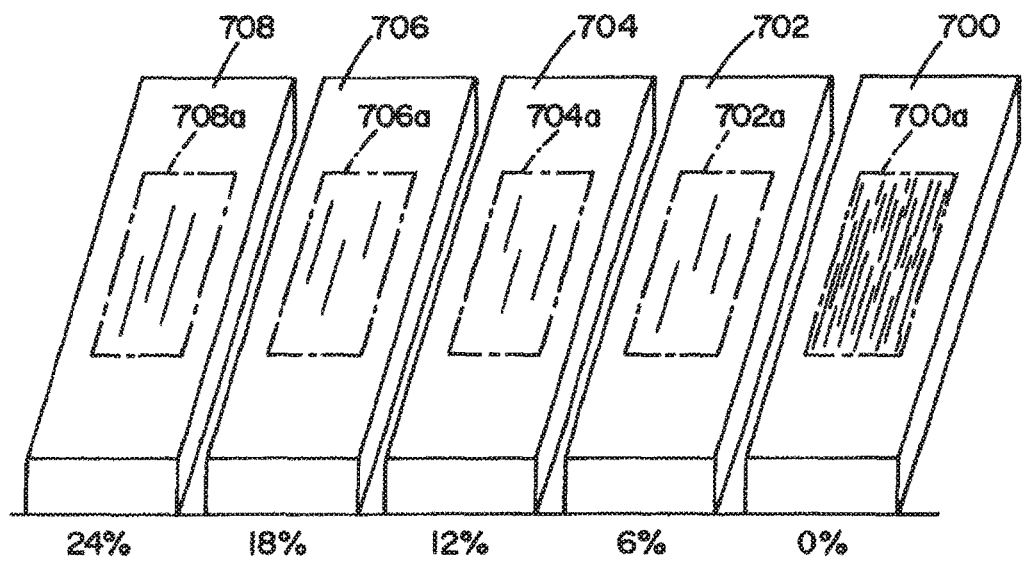

A study was conducted to evaluate the performance of the new ultra fine nepheline syenite powder in a representative clear wood coating formulation. This evaluation was in a standard UV cured water based polyurethane commonly used as a clear coat over wood cabinetry. The study involved collecting data from coatings using product A and product B. Both powders demonstrated significantly improved block and abrasion resistance and had minimal impact on cross hatch adhesion while improving scratch resistance at an optimal loading determined to be 12%. This evaluation for optical clarity gloss hardness and package stability confirmed that there were significant additional advantages for the use of the novel ultra fine nepheline syenite powder. The novel powder offered the best optical clarity, the least haze development, the least settling and a uniform increase in hardness with an increase in loading. The result of this evaluation is the data represented in FIGS. 26, 27 and 28. The coating used in this evaluation was an aqueous UV cured formulation based upon Bayhydrol UV VP LS 2317. This is a polyurethane resin containing an acrylic functional group. The performance of product A and product B in this system as a function of mineral loading between 6% powder and 24% powder gave the results shown in the aforesaid three drawings. Product A had a uniform increase in hardness with increased loading. This attribute of product A is shown in FIG. 26 wherein the hardness data of product A for different loadings is shown as vertical bars 600, 602, 604 and 606. The increase of hardness represented by these bars generally has a linear relationship with respect to the loading percentage increases. This relationship is represented by line x. It was found that increases in the loading of the powder for product B resulted in erratic and unpredictable hardness levels, as represented by the data in vertical bars 610, 612, 614 and 616. Consequently, a user of ultra fine grain and nepheline syenite powder can control hardness of the coating dependably only by using the novel nepheline syenite powder of the present invention. The rate of hardness increase of product A with respect to concentration of powder is, indeed, extremely consistent. This is a distinct advantage in using ultra fine nepheline syenite powder for producing a coating having a distinct hardness specification. It is also important to determine the abrasion level of a coating after it has been cured and has hardened. Thus, the same coating having various percentages of the novel nepheline syenite powder were applied to test panels and allowed to cure or dry. These panels were cut into strips and evaluated for abrasion according to the percentage of nepheline syenite powder in the coating. These strips are schematically illustrated in FIG. 27. Strip 700 has a clear coating without the novel nepheline syenite powder. This novel powder was added to the coating in loading values of 6%, 12%, 18% and 24% as represented by strips 702, 704, 706 and 708, respectively. The coatings on these strips were subjected to a steel wool double rub under a 1500 gram load over approximately a 0.5 inch by 2 inch area. The abrasion results were surprising. They are schematically shown. Rub area 700a of strip 700 had substantial scratches. However, the rub area 702a of strip 702 revealed very minor scratches. Indeed, this same level of scratch resistance was found in rub areas 704a, 706a and 708a of strips 704, 706 and 708, respectively. Consequently, the scratch resistance when using the novel nepheline syenite powder is drastically improved with a minor amount of powder, apparently less than 6% loading. This abrasion resistance is not appreciably changed by adding greater amounts of nepheline syenite powder. Thus, a small amount of novel nepheline syenite powder provides a substantial improvement in abrasion resistance. More powder does not substantially improve this beneficial property. These abrasion test results were verified by the data shown in FIG. 28, which discloses the change of gloss for 50 double rubs at different loadings. The data in FIG. 28 reveals a drastic change in gloss for a clear coating as used on strip 700. This change in gloss is represented by vertical bar 750. The change in gloss for product B for different concentrations in the coating are represented by bars 752b, 754b, 756b and 758b. These changes are substantially greater than the change in gloss for product A which is minor and is obtained primarily by the addition of approximately 6% of powder. The change of gloss data for product A is illustrated by the vertical bars 752a, 754a, 756a and 758a.

Figure 28:
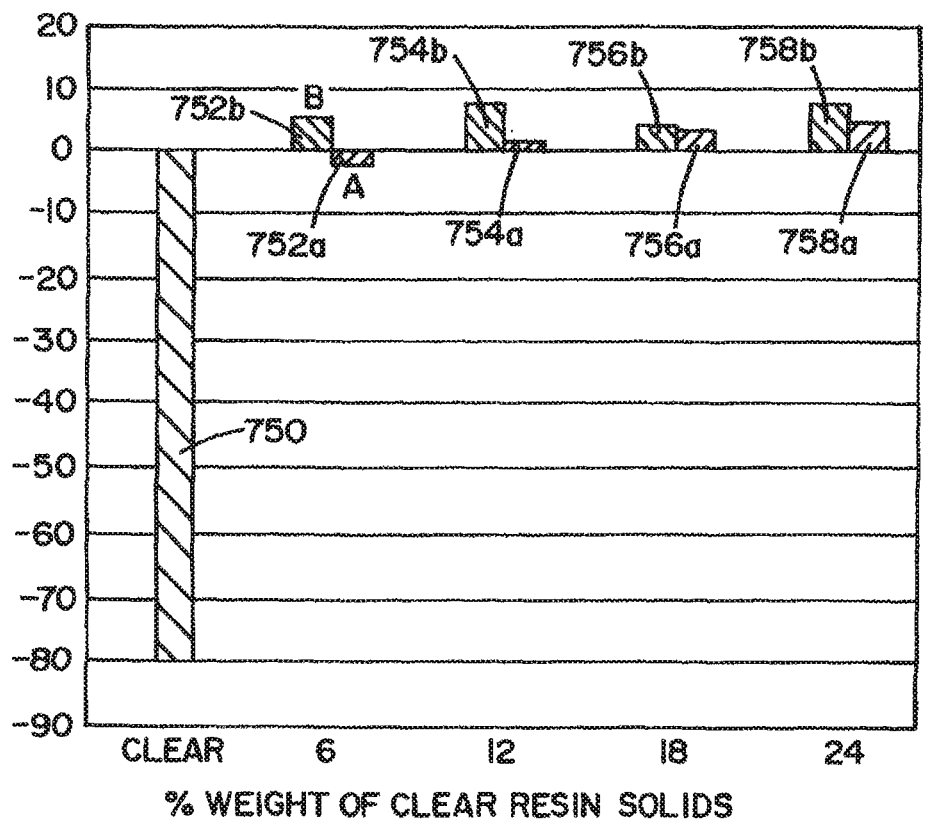

In summary, the novel nepheline syenite powder of the present invention has a consistent uniform change in hardness based upon powder concentration, as shown in FIG. 26. However, the change in concentration does not drastically affect the change in gloss or the abrasion characteristics of the coating as shown in FIGS. 28 and 27, respectively. With these combined features for the novel nepheline syenite powder, the hardness of the coating can be accurately controlled to a precise specification, without regard to a change in the gloss or a change in abrasion of the coating. This combined synergistic relationship obtained by the novel nepheline syenite powder is not obtainable in product B. Consequently, tremendous commercial advantage is obtained by use of the novel nepheline syenite powder. This synergistic advantage is in addition to the drastic reduction in equipment wear and the drastic decrease in settling rate obtainable only by the nepheline syenite powder having a grain size of less than 6 microns.

As a result of this study, it was concluded that an 18% loading of nepheline syenite powder having a particle size of less than 6 microns can be used in the coating with a minimum increase in haze. The 18% loading of this novel nepheline syenite powder results in a modest gloss decrease of about 20 points relative to an unmodified coating as shown in FIG. 28. Larger grain nepheline syenite powder decreases gloss more drastically and gives unpredictable hardness. A minor amount of the novel nepheline syenite powder results in the amount of scratch resistance to be obtained by the powder even at higher loading levels so abrasion resistance and gloss control are not factors in creating the precise hardness required. Consequently, this study establishes several additional advantageous properties of a coating using the novel nepheline syenite powder of the present invention.

Figure 29:
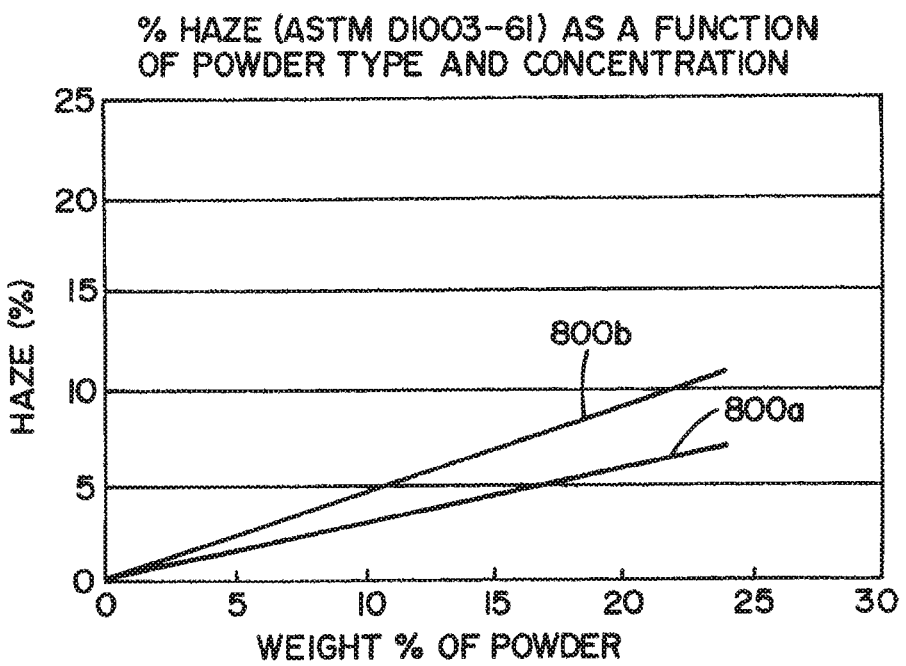
FIG. 29 is a graph illustrating the relationship between percent haze and the weight percentage concentrations of products A and B used in a polyurethane coating.
Figure 30:
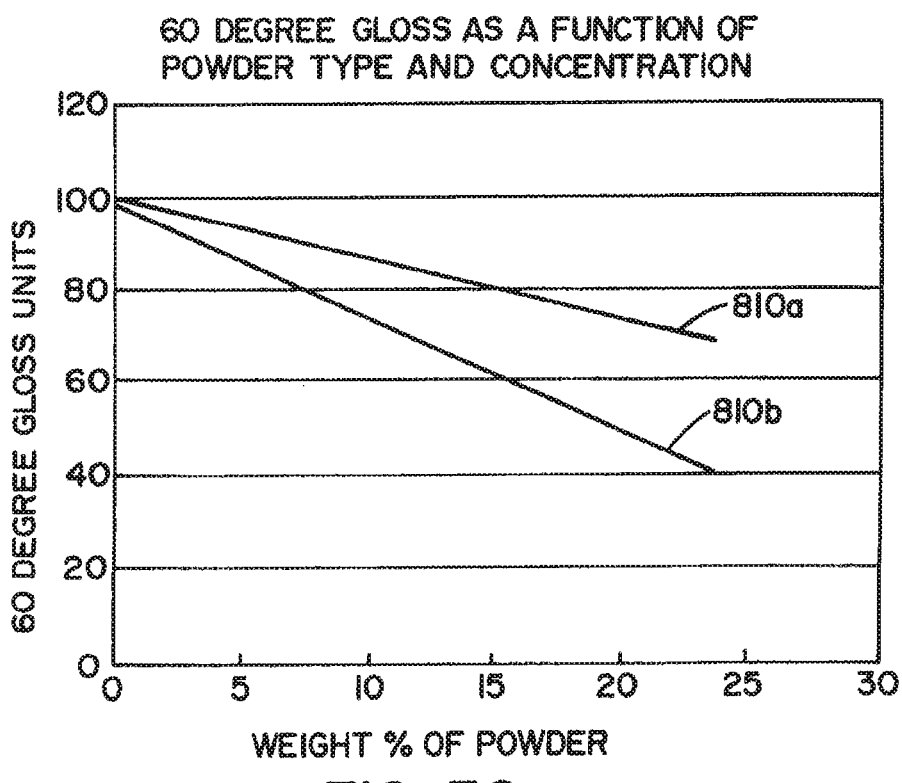
FIG. 30 is a graph illustrating the relationship between gloss units and the weight percentage concentrations of products A and B used in a polyurethane coating.

In yet another series of investigations, the effect of use and incorporation of products A and B into a water-based polyurethane clear coating system was studied. Specifically, an aqueous UV curable formulation based upon Bayhydrol UV VP LS 2317, a polyurethane resin containing acrylic functional groups was prepared. Various samples containing loadings of from 0 to 24% of products A and B were then prepared by incorporating the respective product into the described system. No defoamers or wetting/dispersing agents were used in any of the samples. The various sample formulations were then applied onto substrates and haze and gloss measurements were then made after drying and UV curing of the resulting coating. Specifically, coating samples were air dried for 10 minutes, followed by forced drying at 49° C. for 10 minutes. Samples were then exposed to three passes through an American Ultraviolet UV reactor equipped with a medium pressure mercury lamp house in an elliptical reflector. The lamp wattage was set at 300 WPI, and the belt speed at 25 FPM. The cure energy per pass was measured at 300 mj/cm$^2$ and 0.674 W/cm$^2$ UVA. Haze of the resulting coatings was characterized by ASTM D1003-61 utilizing a Cary 100 spectrophotometer equipped with a 73 mm diameter diffuse reflectance integrating sphere. A blank slide was used when obtaining the baseline and scatter of the instrument. Gloss, i.e. a 60 degree gloss, was determined over the black portion of the chart with a BYK Gardner Tri-Gloss instrument. FIG. 29 illustrates the haze percentage measured from samples of the dried and cured polyurethane coating having various concentrations of either product A, shown by line 800a, or product B, shown by line 800b. FIG. 30 illustrates the gloss measured from the samples. Measurements of gloss from samples with varying concentrations of product A are shown by line 810a. And, measurements of gloss from samples with varying concentrations of product B are shown by line 810b. Referring further to FIGS. 29 and 30, it can be seen for example, that 18% product A may be utilized in this coating with a minimal increase in haze while also providing a significant increase in gloss. Product B additions decrease gloss more dramatically, although the effect of product B additions on haze is not as significant.

Comparison of Product A with Common Fine Grain Fillers

Figure 14:
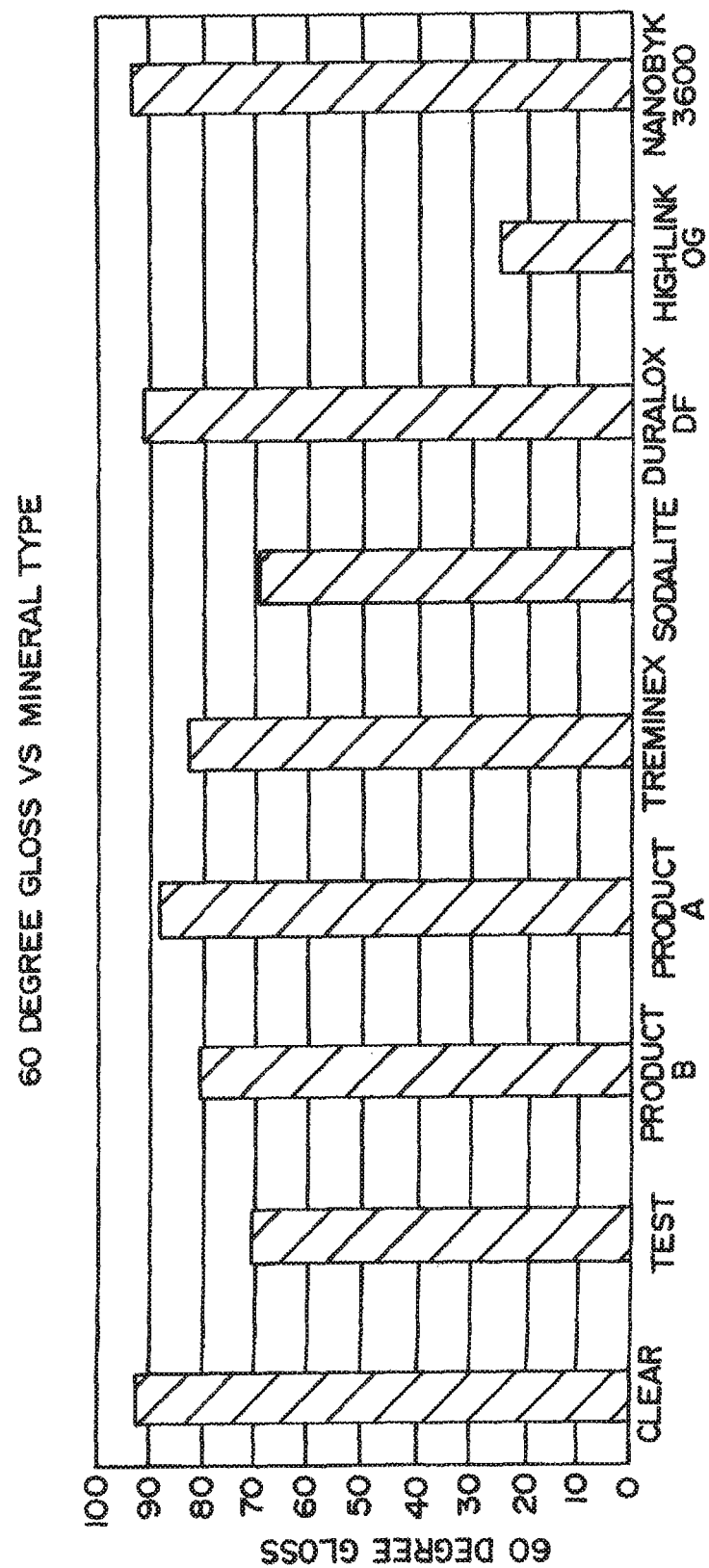
FIGS. 14-25 are vertical graphs comparing a property of a product using product A with the corresponding property of products with other fine grain fillers and additives for which product A is a substitute. These graphs represent data comparing properties which are normally used to show effect of fillers or binders. This array of graphs are used to compare the total functions of the many powders identified.
Figure 15:
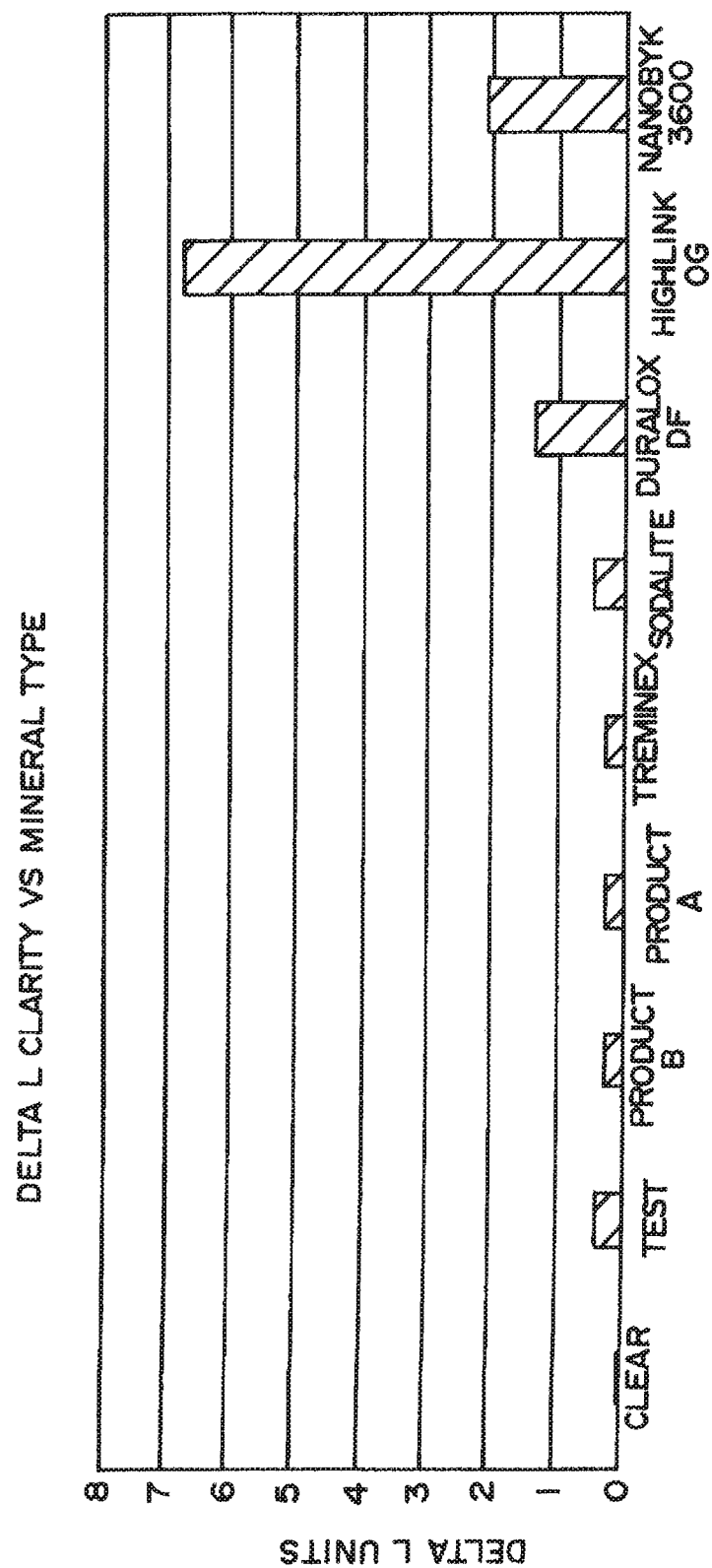
Figure 16:
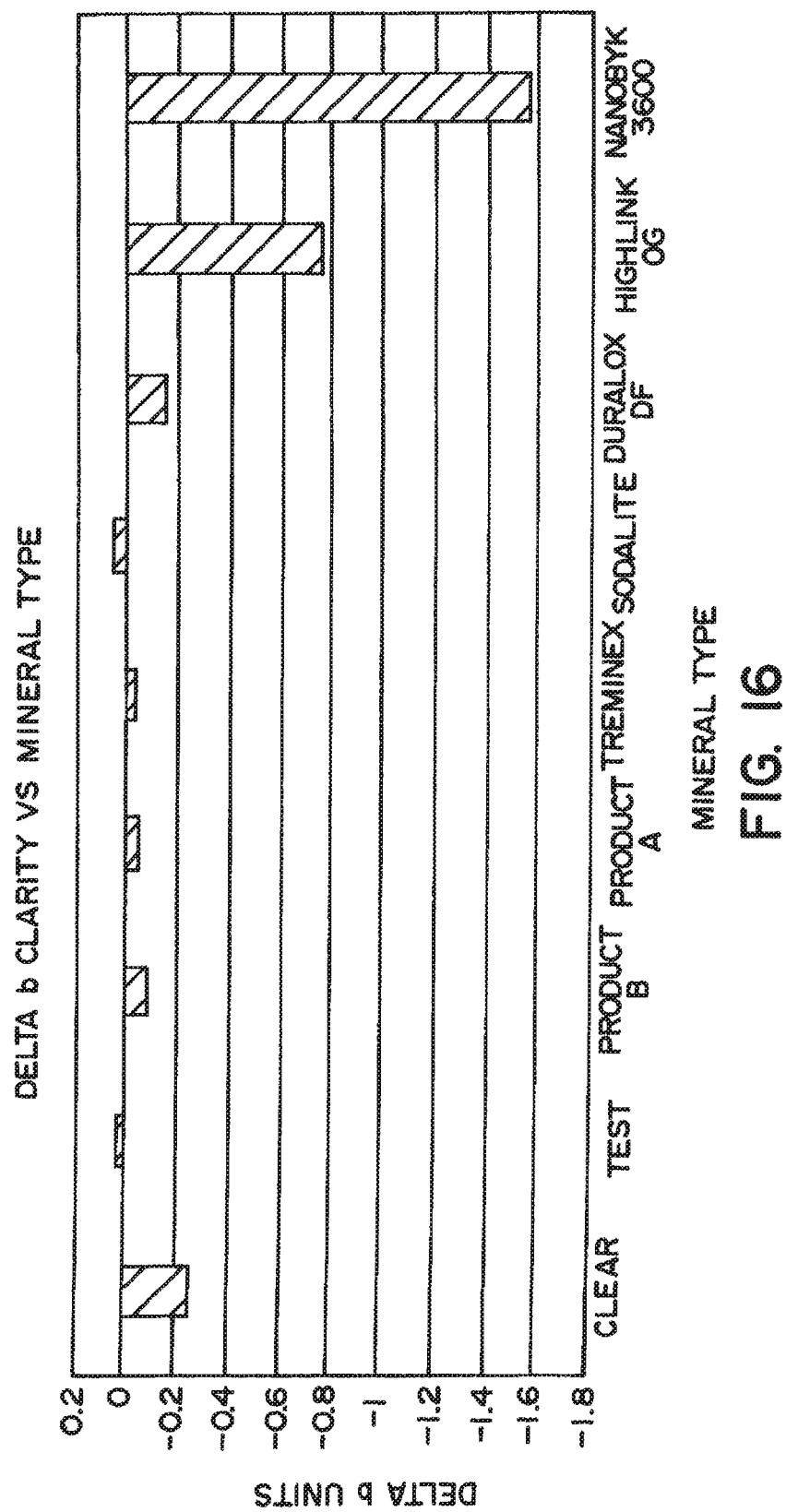

A study was conducted to evaluate the new finer grain ultra fine nepheline syenite powder in aqueous UV formulated coating as compared with commercially available fine grain minerals. The commercial materials to which the nepheline syenite powders were compared are Treminex 958-700 AST, Sodalite 100-90-1, micron sized alumina (Duralox DF 1200), nano sized colloidal silica (Highlink OG 502-31) and NanoByk 3600. The coating volumes were held constant for comparison. The results of the comparison for gloss are represented in FIG. 14. A coating identified as the "test" includes large grain nepheline syenite powder with a grain size above 50-60 microns. Syenite powder with a grain size of less than 15 microns is again identified as product B and is displayed beside the novel nepheline syenite powder (product A) having a grain size of less than 6 microns. Products with nepheline syenite powder show a nearly linear relationship in 60° gloss. Product A results in the greatest gloss. Thus, the data in FIG. 14 is evidence of an advantage obtained by using finer grain ultra fine nepheline syenite powder. The greatest gloss is obtained by the very expensive nano-alumina identified as NanoByk 3000. The distinct advantages of nepheline syenite powder are obtained without substantial reduction in gloss by adopting and using nepheline syenite powder having a grain size of less than 6%. The graphs in FIGS. 15 and 16 show that nepheline syenite powder and Treminex provides the best delta L clarity and the best delta b clarity. This data comparison indicates that ultra fine nepheline syenite powders significantly improved clarity when compared to micron sized alumina, nano sized alumina and nano sized colloidal silica. A smaller delta L value indicates improved clarity. More negative delta b values indicate greater blue haze. Data displayed by the graphs of FIGS. 15 and 16 also reveal that ultra fine nepheline syenite powder is beneficial in the area of clarity for use in coatings. Other commercial fillers are more expensive and are generally less successful in maintaining coating clarity. Indeed, the grain size of the ultra fine nepheline syenite powder is quite important for blue haze clarity of the graph in FIG. 16. Product A is demonstrably better than product B in this physical property. All samples show some degree of impact on visual clarity; however, product A results in the best visual clarity as compared to the unmodified coating. Although nano sized alumina results in good visual clarity upon first inspection, under intense lighting situations, the samples show a large amount of blue haze. This is borne out by the data shown in FIG. 16 and disqualified NanoByk 3600 for some quality intense coatings.

Figure 17:
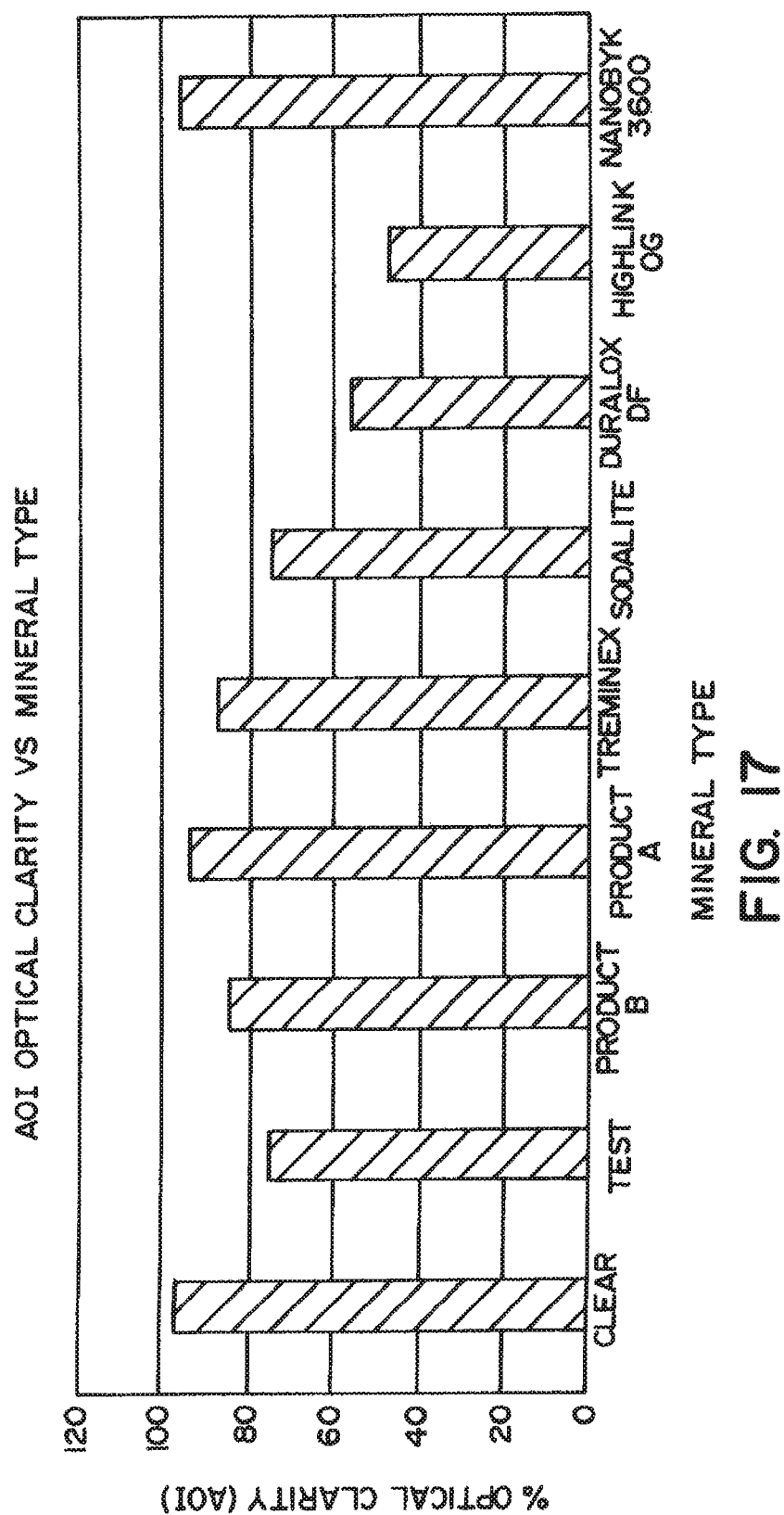

The optical clarity as measured by WCRG's AOI methodology is shown in the graph of FIG. 17. The best optical clarity is given by the unmodified sample, i.e. the "clear" coating sample. This AOI clarity level is followed closely by the levels obtained with nano size alumina. Duralox filler is only slightly better than use of product A as the coating filler. The values of the optical clarity determined by these three products range from about 93% to about 97% indicating a very good clarity for all three of these fillers. The chart also shows that as the size of the nepheline syenite powder increases, the AOI optical clarity decreases. This is an advantage of the use of product A over other nepheline syenite powders because higher loading can obtain the same AOI clarity. This is a tremendous cost saving feature.

Figure 18:
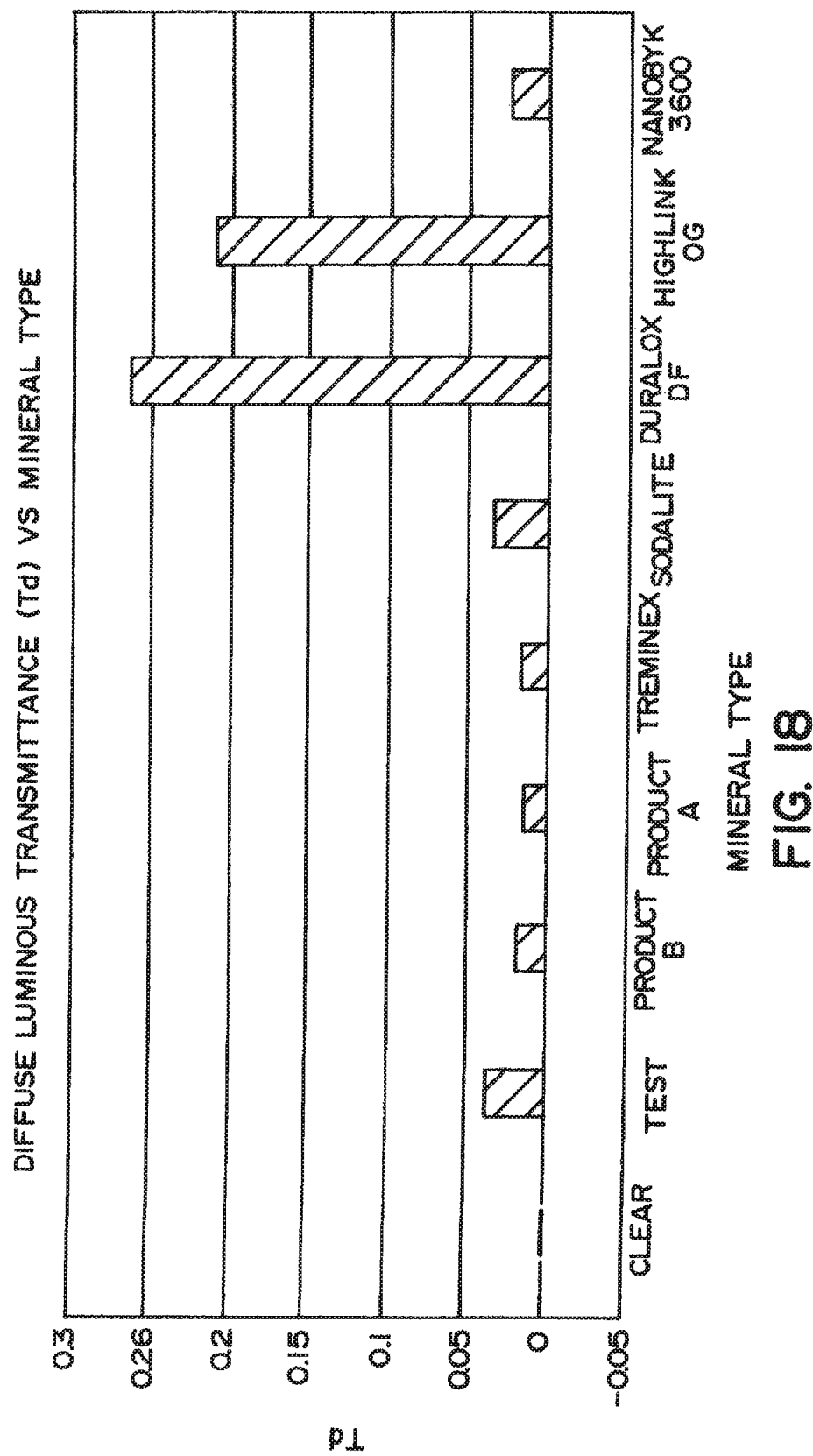
Figure 19:
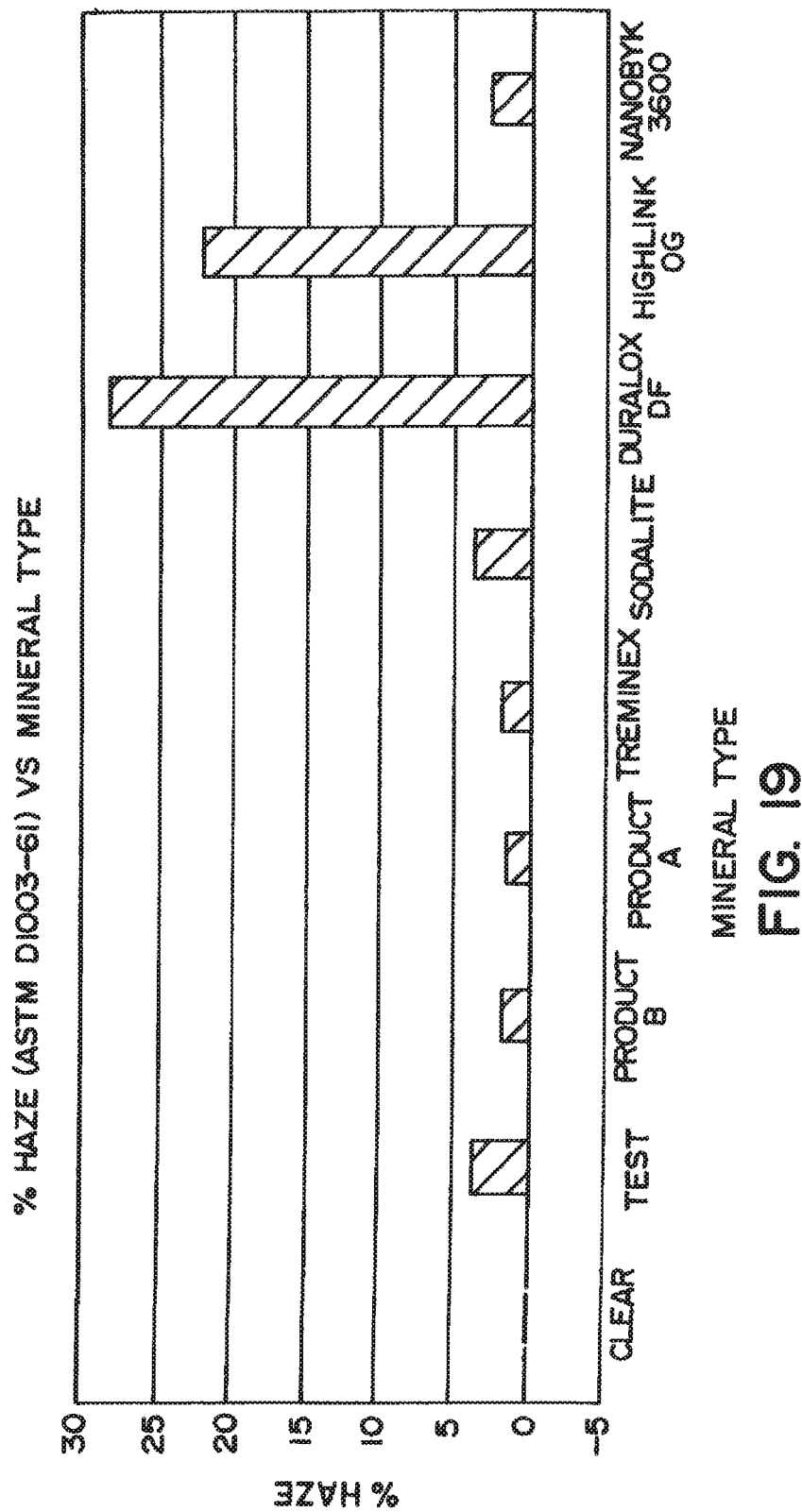

All minerals show some scattering and result in some haze formulation relative to clear, unmodified coating. This observation is disclosed by the graphs of FIGS. 18 and 19. The disclosed values indicate that product A results in the least scattering and haze development of all the minerals tested. This is a substantial advantage for nepheline syenite powder having a grain size less than 6 microns. When the grain size of the nepheline syenite increases as indicated by the "test" sample, the haze drastically increases. The commercially available micron sized alumina results in significant scattering and haze formation. Thus, ultra fine nepheline syenite powder is a substantial improvement in the haze characteristics from the commercially available small grain products and from the "test" sample. The nano sized particles which are extremely expensive are the closest to the inexpensive nepheline syenite powder of product A.

Figure 20:
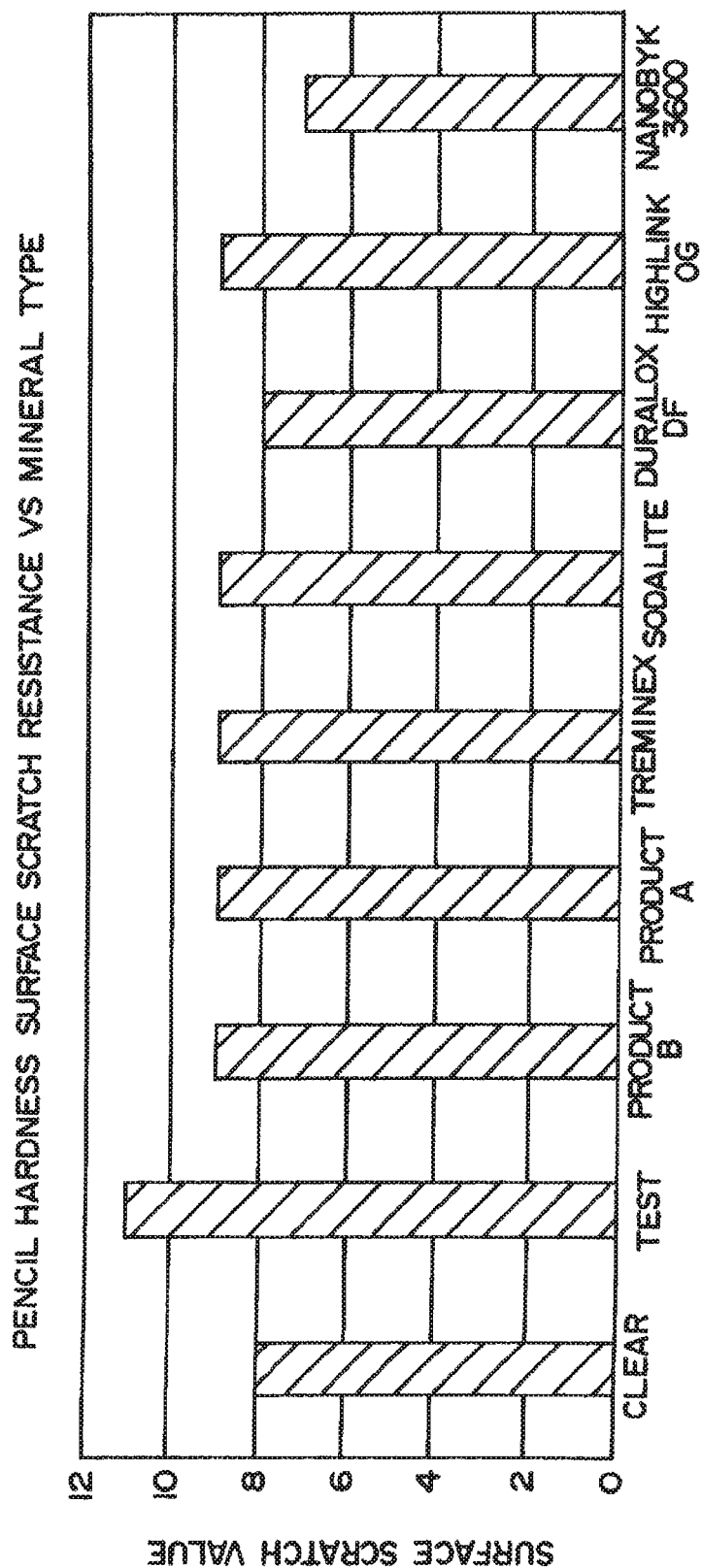
Figure 21:
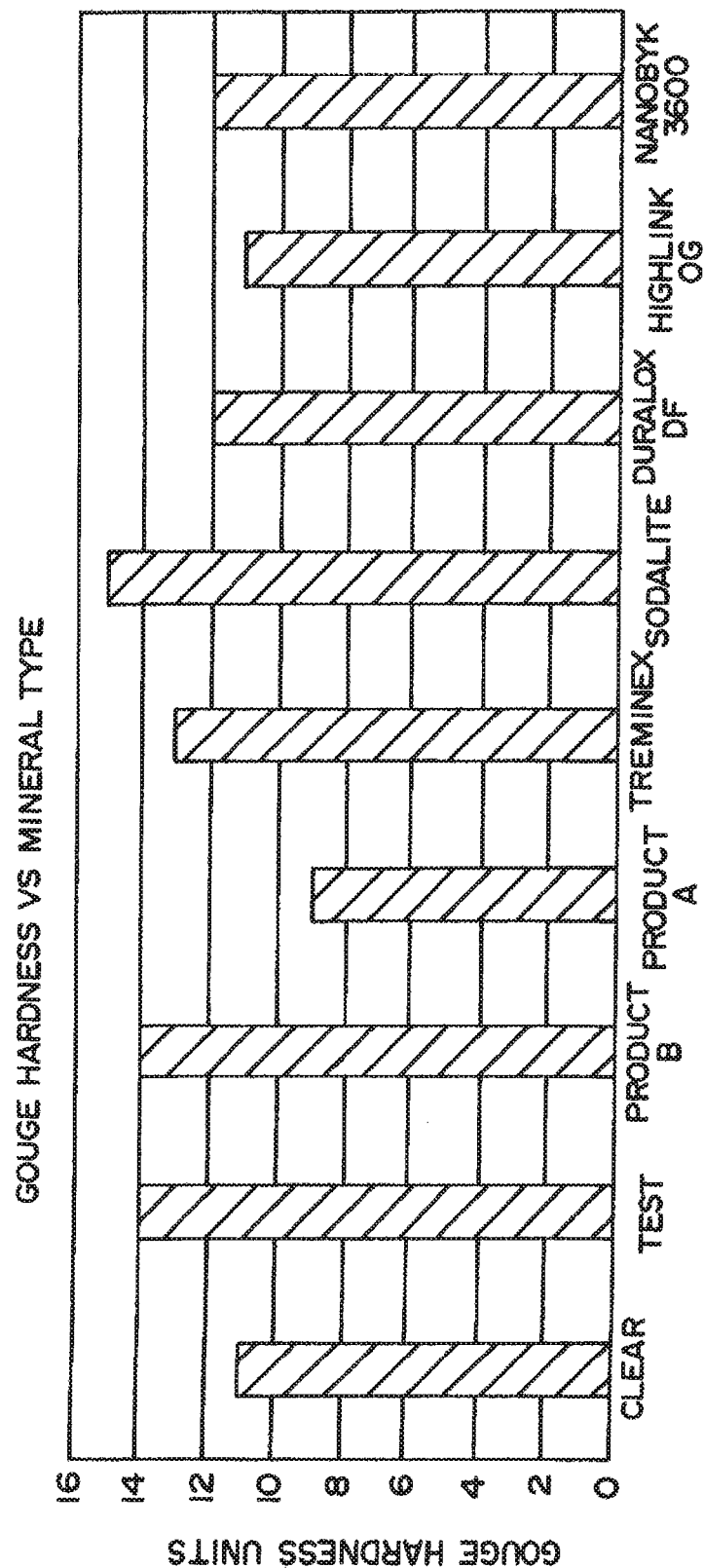

Turning now to FIG. 20, this graph shows that the pencil hardness and surface scratch resistance is improved by decreasing the size of the particles of nepheline syenite powder. In the graph constituting FIG. 21, the coating using Sodalite results in the worst gouge hardness. Product A is substantially advantageous in this particular physical property. However, this property is a minor factor or technical consideration when balanced against the tremendous merits of using the novel nepheline syenite powder in coatings.

Figure 22:
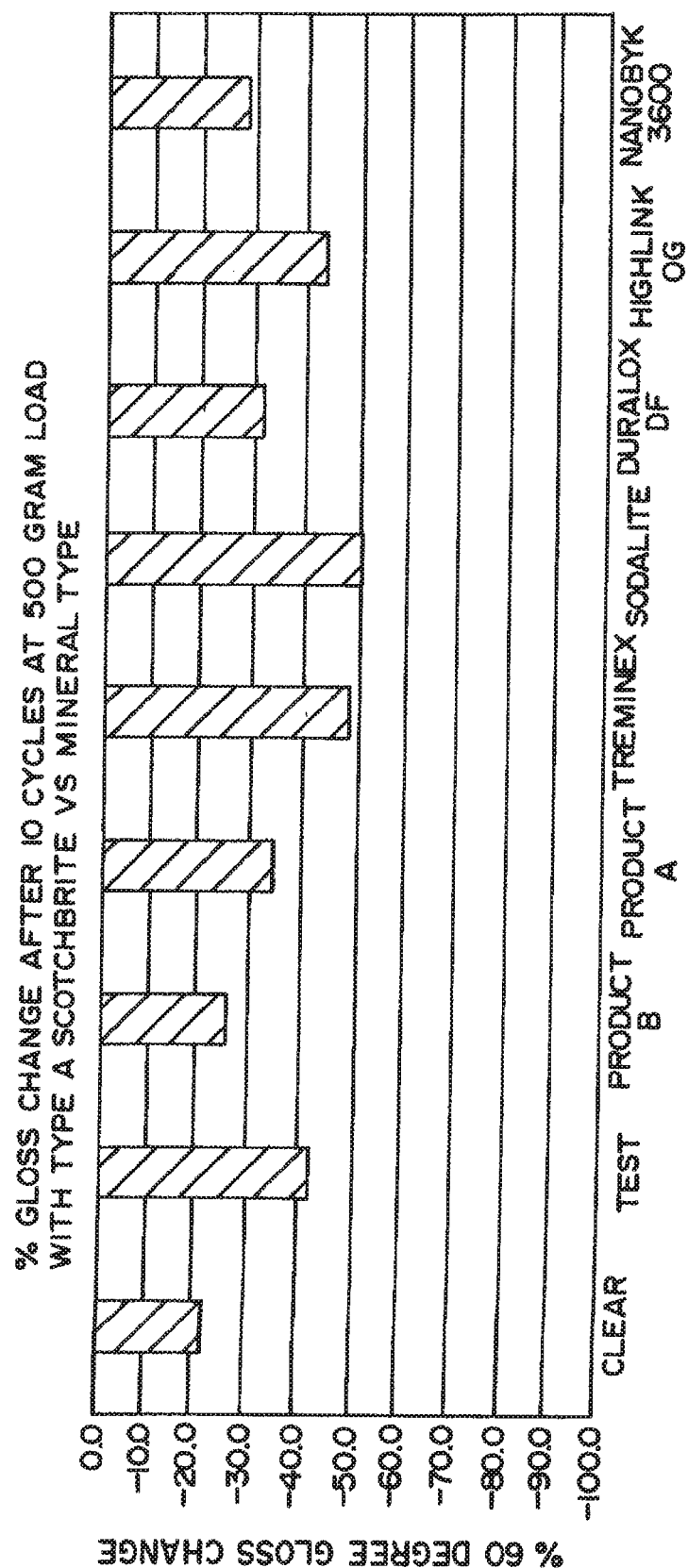
Figure 23:
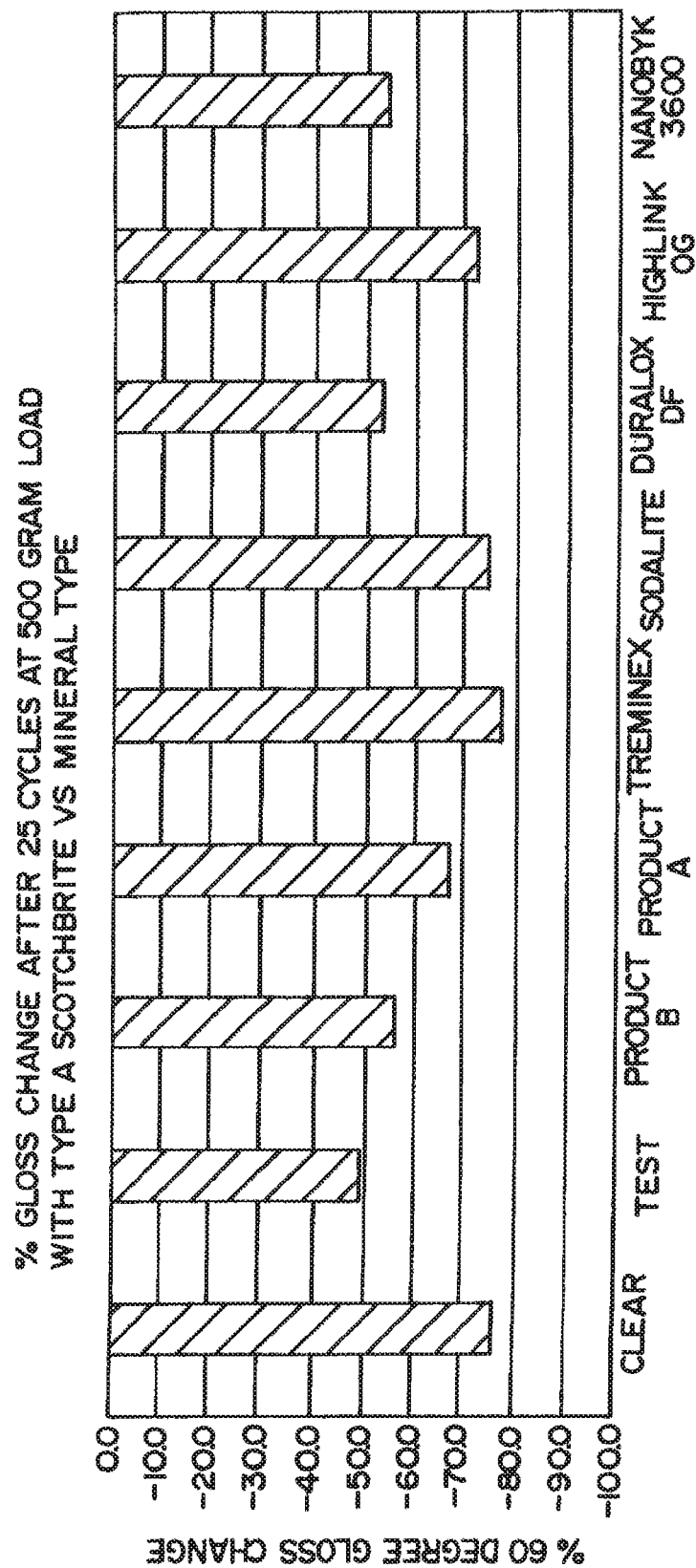
Figure 24:
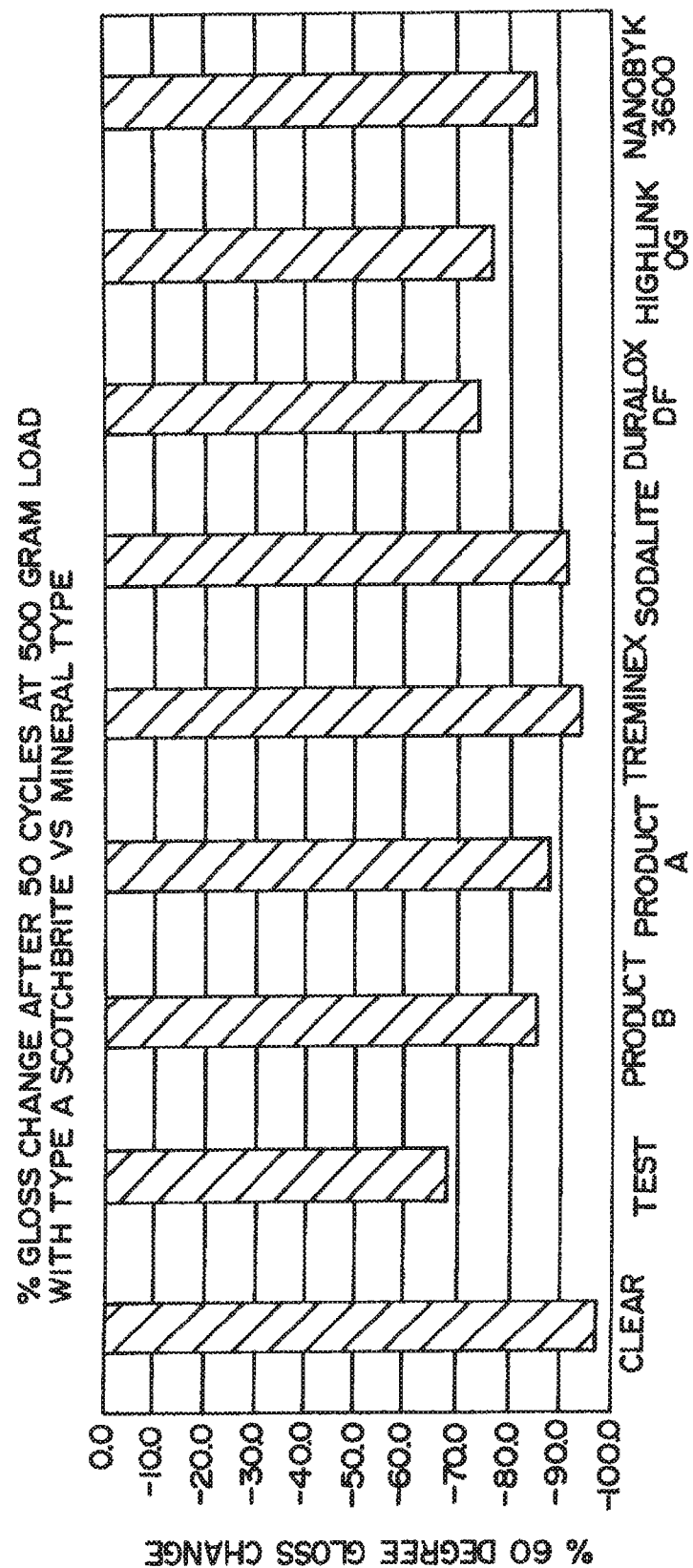
Figure 25:
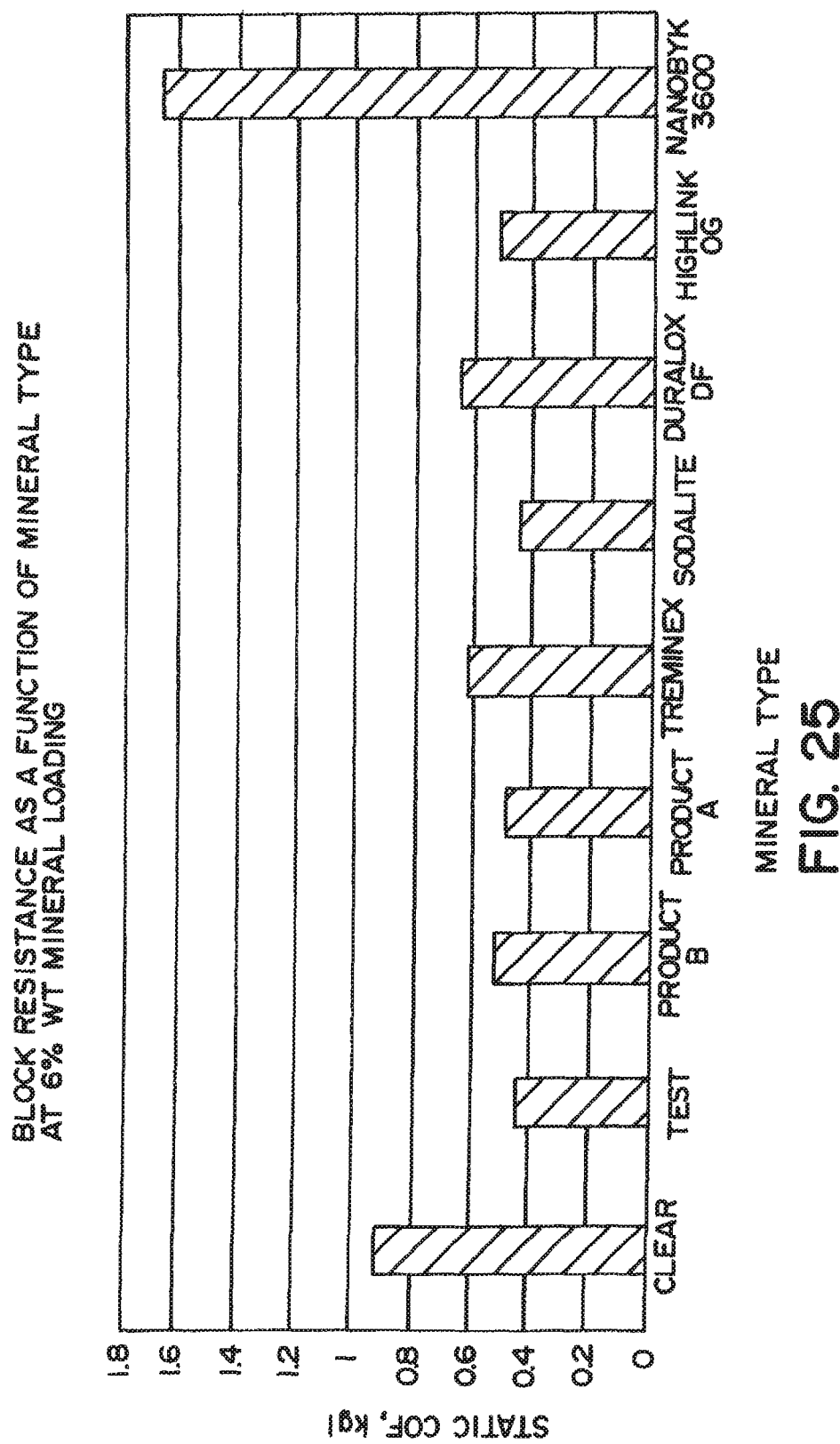

Scratch resistance results indicate some interesting comparisons, as shown by the data contained in the graph of FIG. 22. The unmodified "clear" coating exhibits the worst scratch resistance. Products A and B obtain the good results. Sodalite and Treminex created the least scratch resistance for the samples evaluated at 10 cycles. After 25 cycles, as shown in FIG. 23, the data discloses that the unmodified "clear" coating exhibits a very dramatic decrease in scratch resistance. The "test" coating sample exhibits the least amount of change in scratch resistance and the overall best scratch resistance of all the several samples evaluated. The micro-size and nano-size alumina samples show the next best scratch resistance results after 25 scratch cycles. After 50 scratch cycles, the "test" sample continues to show the best scratch resistance of all the samples as shown by the graph in FIG. 24. The "test" sample is nepheline syenite powder with substantially larger grain size than the ultra fine nepheline syenite powders of product A and product B. Scratch resistance is merely one of many physical characteristics obtained by adding a filler to a coating. The common properties have been evaluated and are illustrated in the graphs of FIGS. 14-25. Lack of hardness as disclosed in the graph of FIG. 24 is not a major consideration in the coatings of products of Table I.

The addition of all the minerals, except the nano size alumina, improves block resistance of the coating. The data on this particular property is shown in the graph presented in FIG. 25. The best block resistance is obtained by nepheline syenite powder having a large grain size as indicated by the "test" sample. Furthermore, the Sodalite minerals also provide good block resistance. Again this characteristic is not a controlling factor for fillers discussed in this section and reported in FIGS. 14-25.

FIGS. 14-25 are somewhat exhaustive in reporting on the physical effect of nepheline syenite powder in a specific coating. They are provided to illustrate that the novel product A has an overall advantage over other nepheline syenite powders and clearly over other fine grain fillers when considering all properties in a total technical analysis. The reported tests were not selected to reveal only properties in which product A excels, but were provided to show the standard array of properties to establish the benefits of the novel nepheline syenite powder. The novel powder, in the totality of property enhancements is a substantial improvement in the art of coating fillers. This fact, combined with its drastic effect on reducing the wear on manufacturing equipment, establishes the substantial merit of drastically reducing the grain size of ultra fine nepheline syenite powder. The novel ultra fine nepheline syenite powder and novel uses of this powder together with novel uses of ultra fine nepheline syenite powder in general have been disclosed.

The exemplary embodiments have been described with reference to the preferred embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

The invention claimed is:

1. A product including fine grain ultra-fine nepheline syenite powder formed from particles where said powder has a controlled maximum particle size with 99.9% of said particles of said powder having a particle size of less than 10 microns, said ultra-fine powder comprising 3-25% by weight of said product and has a moisture content of less than 0.8%, and said product being selected from the class consisting of:
  a) Clear liquid wood coating;
  b) Clear liquid coating for flexible substrates;
  c) Clear liquid coating for rigid substrates;
  d) Nail polish;
  e) Glass;
  f) Metallurgical slag;
  g) Refractory filler; and,
  h) Pigment paste.

2. A product as defined in claim 1 wherein said powder is free of particles having a particle size less than about 0.2 microns.

3. A product including a fine grain ultra-fine nepheline syenite powder formed from particles where said powder has a controlled maximum particle size with 99.9% of said particles of said powder having a particle size of less than 10 microns, said fine grain ultra-fine powder comprising 3-25% by weight of said product and has a moisture content of less than 0.8%, and said product being selected from the class consisting of:
  a) Opaque liquid coating;
  b) A powder filler for a coating;
  c) Powder coatings;
  d) Ceramic bodies;
  e) Glaze
  f) Plastic filler;
  g) Rubber filler; and,
  h) Concentrate.

4. A product as defined in claim 3 wherein said powder is free of particles having a particle size less than about 0.2 microns.

5. A product including a fine grain ultra-fine nepheline syenite powder formed from particles where said powder has a controlled maximum particle size with 99.9% of said particles of said powder having a particle size of less than 10 microns, said fine grain ultra-fine powder comprising 3-25% by weight of said product and has a moisture content of less than 0.8%, and said product being selected from the class consisting of:
  a) Clear coating;
  b) Sealants;
  c) Paper laminates;
  d) Aqueous coating;
  e) Solvent based coating;
  f) UV cured coating;
  g) Water based coating with resin free pigment paste;
  h) Nitrocellulose clear lacquer;
  i) Acrylic lacquer;
  j) Clear solvent based acid cured varnish;
  k) Aqueous lacquer;
  l) Acrylic urethane coating;
  m) Aqueous clear PUD urethane coating;
  n) 100% solid clear UV coating; and,
  o) Concentrate for adding to a final product.

6. A product as defined in claim 5 wherein said powder is free of particles having a particle size less than about 0.2 microns.

7. A coating for a product, said coating comprising a fine grain ultra-fine powder formed from particles of a naturally occurring oxide mineral with no free silica where 99.9% of said particles of said powder having a particle size of less than 10 microns and a moisture content of less than 0.8%, said fine grain ultra-fine powder comprising 3-25% by weight of said coating.

8. A coating for a product as defined in claim 7 wherein said naturally occurring oxide mineral is nepheline syenite.

* * * * *